US006984771B2

(12) United States Patent
Roberds et al.

(10) Patent No.: US 6,984,771 B2
(45) Date of Patent: Jan. 10, 2006

(54) MICE HETEROZYGOUS FOR WFS1 GENE AS MOUSE MODELS FOR DEPRESSION

(75) Inventors: Steven L. Roberds, Ellisville, MO (US); Rita M. Huff, Wildwood, MO (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/195,963

(22) Filed: Jul. 16, 2002

(65) Prior Publication Data

US 2003/0167488 A1 Sep. 4, 2003

Related U.S. Application Data

(63) Continuation of application No. 09/871,107, filed on May 31, 2001, now abandoned.
(60) Provisional application No. 60/209,394, filed on Jun. 1, 2000.

(51) Int. Cl.
    *G01N 33/00*     (2006.01)

(52) U.S. Cl. .................... 800/3; 800/8; 800/9; 800/13; 800/18; 800/21; 800/25
(58) Field of Classification Search .................. 800/3, 800/8, 9, 13, 21, 25, 18, 14, 24
    See application file for complete search history.

(56) References Cited

U.S. PATENT DOCUMENTS

| 4,736,866 A | 4/1988 | Leder et al. ................. 800/1 |
| 4,873,191 A | 10/1989 | Wagner et al. ............ 435/172.3 |
| 5,166,065 A | 11/1992 | Williams et al. .......... 435/240.1 |
| 5,354,855 A | 10/1994 | Cech et al. ................ 536/24.1 |
| 5,449,620 A | 9/1995 | Khillan ....................... 435/284 |
| 5,453,357 A | 9/1995 | Hogan ...................... 435/7.21 |
| 5,670,372 A | 9/1997 | Hogan ..................... 435/240.2 |
| 5,753,506 A | 5/1998 | Johe .......................... 435/377 |
| 5,985,659 A | 11/1999 | Kusakabe et al. .......... 435/354 |

FOREIGN PATENT DOCUMENTS

| WO | WO 00/18787 | * | 4/2000 |
| WO | WO 00/18787 |   | 6/2000 |

OTHER PUBLICATIONS

Babinet, J. Am. Soc. Nephrol. 11: 588–594, 2000.*
Crabbe et al., Science, 284, 1670–1972, 1999.*
Sigmund, Arterioscler Thromb Vasc. Biol. 20:1425–1429, 2000.*
Phillips et al., Pschopharmacology, 147:5–7, 1999.*
Crawley et al., Psychopharmacology 132: 107–124, 1997.
Steinberg, The Scientist, 17:1–6, 2003.
Bilbo, Lab Animal, 30, 24–29, 2001.
Hardy et al. Am. J. Hum. Genet. 65:1279–1290, 1999.
Ohtsuki et al., Journal of Affectice Disorders 58: 11–17, 2000.
Strom et al. Human Molecular Genetics, 1998, vol. 7, pp. 2021–2028.*
Strojek et al. Genetic Engineering: Principles and Methods, Plenum Press, 1988, vol. 10, pp. 221–246.*
Nulman et al. The New England Journal of Medicine, 1997, vol. 336, pp. 258–262.*
Mullins et al. J. Clin. Invest, 1996, vol. 97, pp. 1557–1560.*
Hodebine, Journal of Biotechnology, vol. 34, 1994, pp. 269–287.*
Wall, Theriogenology, 1996, vol. 45, pp. 57–68.*
Rulicke et al. Experimental Physiology, 2000, vol. 85, pp. 589–601.*
Polejaeva et al. Theriogenology, 2000, vol. 53, pp. 117–126.*
Humpherys et al. Science, 2001, vol. 293, pp. 95–97.*
Bishop, Reprod. Nutr. Dev. Vol. 36, 1996, pp. 607–616.*
Chiu et al. Folding & Design, 1998, vol. 3, pp. 223–228.*
Russell et al. J. Mol. Biol. 1994, vol. 244, pp. 332–350.*
Gerhold et al. Bioessays, 1996, vol. 18, pp. 973–981.
Swift, et al., "Psychiatric Disorders And Mutations At The Wolfram Syndrome Locus", 2000 Society of Biological Psychiatry, 787–793.
Strom, et al., "Diabetes Insipidus, Diabetes Mellitus, Optic Atrophy And Deafness (DIDMOAD) Caused By Mutations In A Novel Gene (Wolframin) Coding For A Predicted Transmembrane Protein", Human Molecular Genetics, 1998, vol. 7, No. 13, 2021–2028.
Altschul et al., "Gapped Blast and PSI–Blast: a new generation of protein database search programs", *Nucleic Acids Research*, 25:3389–3402 (1997).
Baichwal and Sugden, "Vectors for Gene Transfer Derived from Animal DNA Viruses: Transient and Stable Expression of Transferred Genes", In: Gene Transfer, Kucherlapati R., ed., New York, Plenum Press,Chapter 5, 117–148 (1986).
Bitter et al., "[33] Expression and Secretion for Yeast" *Methods in Enzymol.*, 153:516–544 (1987).
Brinster et al., "Factors affecting the efficiency of introducing foreign DNA into mice by microinjecting eggs", *Proc. Nat'l Acad. Sci.* (*USA*), 82:4438–4442 (1985).

(Continued)

*Primary Examiner*—Joseph Woitach
*Assistant Examiner*—Brian Whiteman
(74) *Attorney, Agent, or Firm*—Pharmacia & Upjohn Company; Thomas A. Wootton

(57) ABSTRACT

The present invention describes a recombinant rodent model for depression. More particularly, the rodent comprises cells expressing mutations in the WFS1 gene. The rodent is preferably a mouse heterologous for mutations in exon 8 of the WFS1 gene. Preferably, the mutations yield a non-functional wolframin protein that lacks all or some of it transmembrane regions. Methods and compositions for making and using the mouse and cells thereof are disclosed.

32 Claims, 2 Drawing Sheets

OTHER PUBLICATIONS

Bronson and Smithies, "Altering Mice by Homologous Recombination Using Embryonic Stem Cells", *J. Biol. Chem.*, 269(44):27155–27158 (1994).

Cane et al., "Harnessing the Biosynthetic Code: Combinations: Permutations, and Mutations", *Science*, 282:63–68 (1998).

Cech et al., "In vitro Splicing of the Ribosomal RNA Precursor of Tetrahymena: Involvement of a Guanosine Nucleotide in the Excision of the Intervening Sequence", *Cell*, 27:487–496 (1981).

Dymecki, "Flp recombinase promotes site–specific DNA recombination in embryonic stem cells and transgenic mice", *Proc. Nat'l Acad. Sci. USA*, 93:6191–6196 (1996).

Dymecki, "A modular set of Flp, FRT and lacZ fusion vectors for manipulating genes by site–specific recombination", *Gene*, 171(2):197–201 (1996).

Forster and Symons, "Self–Cleavage of Plus and Minus RNAs of a Virusoid and a Structural Model for the Active Site", *Cell*, 49:211–220 (1987).

Forster and Symons, "Self–Cleavage of Virusoid RNA Is Performed by the Proposed 55–Nucleotide Active Site", *Cell*, 50:9–16 (1987).

Gamache et al., *Neurosci. Abstracts*, 17:985 (1991).

Gerlach et al., "Construction of a plant disease resistance gene from the satellite RNA of tobacco ringspot virus", *Nature (London)*, 328:802–805 (1987).

Gossen and Bujard, "Tight control of gene expression in mammalian cells by tetracycline–responsive promoters", *Proc. Nat'l Acad. Sci. (USA)*, 89:5547–5551 (1992).

Gossen et al., "Transcriptional Activation by Tetracyclines in Mammalian Cells", *Science*, 268:1766–1769 (1995).

Houston and Banks, "The chemical–biological interface: developments in automated and miniaturised screening technology", *Curr. Opin. Biotechnol.*, 8:734–740 (1997).

Inoue et al., "A gene encoding a transmembrane protein is mutated in patients with diabetes mellitus and optic atrophy (Wolfram syndrome)", *Nature Genetics*, 20:143–148 (1998).

Joyce, "RNA evolution and the origins of life", *Nature*, 338:217–224 (1989).

Kasahara et al., "Role of 5–HT$_{1A}$ Receptors in the Forced Swimming Wheel Test in Reserpine–Treated Mice", *Life Sciences*, 52:1741–1749 (1993).

Kim and Cech, "Three–dimensional model of the active site of the self–splicing rRNA precursor of *Tetrahymena*", *Proc. Nat'l Acad. Sci.*, 84:8788–8792 (1987).

Ludwig et al., "FLP–mediated site–specific recombination in microinjected murine zygotes", *Transgenic Research*, 5:385–395 (1996).

Macejak and Sarnow, "Internal initiation of translation mediated by the 5' leader of a cellular mRNA", *Nature*, 353:90–94 (1991).

Martin, "Isolation of a pluripotent cell line from early mouse embryos cultured in medium conditioned by teratocarcinoma stem cells", *Proc. Nat'l. Acad. Sci. (USA)*, 78:7634–7638 (1981).

Michel and Westhof, "Modelling of the Three–dimensional Architecture of Group I Catalytic Introns Based on Comparative Sequence Analysis", *J. Mol. Biol.*, 216:585–610 (1990).

Myers, "Will combinatorial chemistry deliver real medicines?", *Curr. Opin. Biotechnol.*, 8:701–707 (1997).

Nicolas and Rubenstein, "Retroviral Vectors", In: Vectors: A survey of molecular cloning vectors and their uses, Rodriguez & Denhardt (eds.), Stoneham: Butterworth, Chapter 25, 493–513 (1988).

Nomura et al., "A New Behvarioral Test for Antidepressant Drugs", *Eur. J. Pharmacol.*, 83(3–4):171–175 (1982).

Nomura et al., *Yakubutsu Seishin Kodo*, *Jpn. J. Psychopharmacol.*, 12:207–213 (1992).

O'Gorman et al., "Recombinase–Mediated Gene Activation and Site–Specific Integration in Mammalian Cells", *Science*, 251:1351–1355 (1991).

Owen, "Psychiatric disorders in Wolfram syndrome heterozygotes", *Mol. Psychiatry*, 3:12–13 (1998).

Palmiter et al., "Dramatic growth of mice that develop from eggs microinjected with metallothionein–growth hormone fusion genes", *Nature*, 300:611–615 (1982).

Pelletier and Sonenberg, "Internal initiation of translation of eukaryotic mRNA directed by a sequence derived from poliovirus RNA", *Nature*, 334:320–325 (1988).

Porsolt, "Behavioural Despair in Rats: A New Model Sensitive to Antidepressant Treatments", *Eur. J. Pharmacology*, 47:379–391 (1978).

Reinhold–Hurek and Shub, "Self–splicing introns in tRNA gnes of widely divergent bacteria", *Nature*, 357:173–176 (1992).

Ridgeway, "Mammalian Expression Vectors", In: Rodriguez R.L., Denhardt D.T., ed. Vectors: A survey of molecular cloning vectors and their uses. Stoneham: Butterworth. Chapter 24, 467–492 (1988).

Sarver et al., "Ribozymes as Potential Anti–HIV–1 Therapeutic Agents", *Science*, 247:1222–1225 (1990).

Sauer, "[53] Manipulation of Transgenes by Site–Specific Recombination: Use of Cre Recombinase", *Methods Enzymol.*, 225:890–900 (1993).

Sauer, "Inducible Gene Targeting in Mice Using the Cre/lox System", *Methods:* A comparison to Methods in Enzymology, 14:381–392 (1998).

Scanlon et al., "Ribozyme–mediated cleavage of c–fos mRNA reduces gene expression of DNA synthesis enzymes and metallothionein", *Proc. Nat'l. Acad. Sci. (USA)*, 88:10591–10595 (1991).

Scharf et al., "6 Heat Stress Promoters and Transcription Factors", *Results Probl. Cell Differ*, 20:125–162 (1994).

Steru et al., "The tail suspension test: A new method for screening antidepressants in mice", *Psychopharmacology*, 85.367–370 (1985).

Steru et al., "The Automated Tail Suspension Test: A Computerized Device Which Differentiates Psychotropic Drugs", *Prog. Neuro–Psychpharmacol. & Biol. Psychiatry*, 11:659–671 (1987).

Swift et al., "Predisposition of Wolfram syndrome heterozygotes to psychiatric illness", *Mol. Psychiatry*, 3:86–91 (1998).

Swift et al., "Psychiatric Disorders in 36 Families With Wolfram Syndrome", *Am. J. Psychiatry*, 148:775–779 (1991).

Temin, "Retrovirus Vectors for Gene Transfer: Efficient Integration Into and Expression of Exogenous DNA in Vertebrate Cell Genomes", Gene Transfer, Kucherlapati (ed.), New York: Plenum Press, Chapter 6, 149–187 (1986).

Teste et al., "Anti–immobility activity of different antidepressant drugs using the tail suspension test in normal or reserpinized mice", *Fundam. Clin. Pharmacol.*, 7:219–226 (1993).

Torres, "The Use of Embryonic Stem Cells for the Genetic Manipulation of the Mouse", *Curr. Top. Dev. Biol.*, 36:99–114 (1998).

Williams et al., "Embryonic Lethalities and Endothelial Tumors in Chimeric Mice Expressing Polyoma Virus Middle T Oncogene", *Cell*, 52:121–131 (1988).

* cited by examiner

SEQUENCE LISTING

<160> NUMBER OF SEQ ID NOS: 13

<210> SEQ ID NO 1
<211> LENGTH: 10917
<212> TYPE: DNA
<213> ORGANISM: Mus musculus
<220> FEATURE:
<221> NAME/KEY:
<222> LOCATION:
<223> OTHER INFORMATION: m=a or c;  w=a or t;  y=c or t;  n=g, a, c or t

<400> SEQUENCE: 1

```
gctaaactcc tggtgtcagc tcagcaggtc tacccaggga tatggacctt tgaatatgat      60
gagactccag gccatgtaat tcctgagcac agtgctagcc caggatccta aggttctatg     120
cccagtgggc tacagagcag gtcaattcag cagcccagc ttctaatcct ctctggtcta     180
gcagatggag gggcgcagcc aggcccagtc cccaagtccc tgcagaagaa gaggcgcatc     240
atggagcgcc tcgtcaccag tgaatgtgag tatgtctgtc gtgttgtgcg atcgtgcttc     300
ccgcacacca cccagcgccg catccctctt aactgtgtgc cctagcctgg ctcccattac     360
atggtgccat ggtttaatgg actcttgttc agtctcattg ggtgacagtg tttggtccct     420
ggtgcataag cctttgccag tggaggtttc agatgacagt ggacacattc attcagtgtg     480
accatcctct acaggtgaag gccagaggcg gggctggtgc ctgagtgagc tgaaaggtca     540
gtgagagaga cagctctaca gataggcagg aggggacttg agggttgtgt ggggtgtgtc     600
ccactgcgca cttgtgttga ggcagatata gagtgttaca gcacccgtgt gggatggaga     660
gggactgggg acccagggag ctggaagtgg ccgtgaaatg tctggggtca gagaatcaga     720
agacactaga ccatgacttc atgtgtgtgt catgtgtgtg gagggtgga atctgtttct     780
```

| | |
|---|---|
| agggctccag gcttccatcc tggagaagat gggcaggtag gggagggggct taggggcttc | 840 |
| tcagcactga taggagagcc cagtgggtgg gacagggctg cacagttctg actcatcatg | 900 |
| ttaactcccg agtgcagcct ctgcaagcaa cctagcccag tgagagcttc aacatggcc | 960 |
| agggctctcg gtgactgccg gtgcctagca ttttttcttcc ctgaaggctg ggaacccagt | 1020 |
| cttttaacaca tgctatattt cttttacccg tccttggcat ttcccagtgc ttcaaaaaaa | 1080 |
| aaaaacaaaa caaaaacaaa caaaaaaaaa aacgtccatt gcataggagg ctcttggcag | 1140 |
| agacaggtga gatagagagg tttgcagaca cacagtggat cctcaaggga tcctggtggg | 1200 |
| ggtgggaaca aaaggcagac ctatgttgcc cttgtatcaa tgctgtgaga tgagagcttg | 1260 |
| gtggcacatg agagatcttg ttgggtggag aagttattgg gtgtgtagta ggtcttttgg | 1320 |
| gggtcagaga atagcagtcc cacagatcct gttgtatggg gggtggcctc ggggaagtta | 1380 |
| gtccccagca tcccaaggcc ctgcatgtcc accaggcatc aaagtatgct ggggtgcagc | 1440 |
| tgattggctg tctagcagta gggcttcgct taaggtgggc tttaggcatt ggggactaga | 1500 |
| agggcatgtc atttcacaca catagcgtgt tgcctaggtc agaagcagag atgggggata | 1560 |
| acagatggca gacaaactac ttcctccaca cccaaacagg ttcttttttca tgtctttgcc | 1620 |
| tgagcgatgg ccctgtgcct gaacctggct gggccccaag ttgccatcct gtgtcctgcg | 1680 |
| tgtatcaggg tcacagtggg tgtatggctt ggagaacccg gtatcttttt gtgctttcag | 1740 |
| ccaagaacta cattgctctg gacgattttg tggagctcac caaaaagtac gccaagggca | 1800 |
| tcattcccac caacctgttc ctgcaggatg aggatgaaga tgagnacgag ctggcaggga | 1860 |
| agagccccga ggacctgcca ctacgccaga aggtatgtgc cgctcctgcc tggcaccctg | 1920 |
| gctcgcccct gggagctgca ggccagaggc ccttanccte acagacacac ctggatntgg | 1980 |
| gtccctcagg tcatctgagg ttcctgtttg anaaggtgcc tcggcccaga aagcagaggc | 2040 |
| agggtcatac aggtatactt gggtgctccg gagagtcatg tcaggacagc agaacttaca | 2100 |
| tttagattca ctatgtagtg atgttatctg tggcccagga cagaggccac tttctaaata | 2160 |
| tgctttcccc cctccaatca agtgctggtc tgtgggccag ctcagtcatg ggcctggtga | 2220 |
| ctgaatctac catacaggga caccaaaggt gagctggaag aacagacatt ggcgggagac | 2280 |
| acaagaatag gagggattta gaagtgtacc ctgctttgac cagtctccac attgttgttg | 2340 |
| ggactcagtg cagacacagg tgtggccata gggccattac agagctgccc aggtcagttt | 2400 |
| atgaacctgg tcagatgtgt ccatagctcg gactgcaggg atgcaagcat ccctgggtat | 2460 |
| tgattgggca ggttgaccca gggaagcact tcagcccagc gtgggcacaa ggccaagccc | 2520 |
| acgcagggcc taacagcaga ggaactgttc tgtagcccat agctctgcag gcctcagtgc | 2580 |
| cagtgtttat ggctaagacg acatgaacca cacacaccag taagactgga caactaggt | 2640 |
| taaaatgggg gcagccgggt ccactggcta ggaagtggcc agacagtctt cacaggggc | 2700 |
| tggagagtaa agcaggccac cacgggggcat gggacacag gacagaagta agaaagtggg | 2760 |
| gagcagctcc ccacaacaga gagataaggc ccgtgtgtga ccgcacccc caggttgttg | 2820 |
| acaggtagag cctcactctt ggccctgagc acagacaggg aaaggactga tactgggaaa | 2880 |
| gttctgagca tcgggctggc ctagaggctc gtggctgtgg gacggtcca tgttcagctt | 2940 |
| ctctagactg agtgtgttcg cagacaggat tcccagatga tgctcgcccc tgagaggagg | 3000 |
| gagctggcgg ggtccgtatg gttcttggca agaagagcc ccacacttgc tagtggggat | 3060 |
| caaggtgaaa ggatgtgttg gagaggaacc ttcaggccag agctttccag tgtgcactgt | 3120 |
| gatgcctcct cccgccacac gaggtctgaa tgtgtgtcct gccaccccac agtgatgtgc | 3180 |

```
ctgagctctg tgaggtctgg aagtgctttg aggagagaga gatttaaagt ctgtgcggag    3240
atcaatgtgg ccccgtgtcg cagtgtttgg aaccatccca gacacggcca gtcacggccg    3300
gtcttttgta gagaaagagc agcaagtcct cacaggggtc tgcacattca agctccctca    3360
gccctccgtg ccttgccttc aagggacatg caggggacgg agaggctcct ctcagtcaca    3420
gccagcagcc tctgagaact gacgtgactc ccgcaaagag tgttctagac tcccaacagc    3480
ttccctcaag cctggggagt cagggtgacc tcttaaaaac aaatttaatg ttttaaagtc    3540
ctgtatgttt tacattcact tatggagaat ctgatgtggc catttcctct caggtttcag    3600
cggaagctgg cttcccacca cttgcctctg tgtgccggg tgacggtggc cgtgctccct    3660
gttagcttgg gttgcagtgt tctgatcacc agtgtcagag ggagggcggg gctctgagct    3720
ccctggactc cccgaccagc cttctttggt gctcatgctg cacctgtatg tgacatgcca    3780
tgtggcctgg gatataatgg ctcccatccc tctggcagtt gaggaaagag tcagtgttgg    3840
tgtccacatg ctggagatgg acacgtggct gatgggcaac ccaatgctgt tgtatctttt    3900
tattttattt ttttaatttt ttttgcaggt aggggaagg gcttcaagac agggtttctc    3960
tgtagagtcc tggccacttt ggaactcact ctgtagacca ggctggcctc aaactcagag    4020
atccacctgc ctctgcctcc caagtgctgg gattaaaggt gtgtgcccaa ccacctggc    4080 gtgatattgt atcttgaagc aggagatggg gatctaggtg cccaggtggc ttcccctaga    4140
tgcaataggc ttgtgcaagt ccctagtcac cttagcagaa ggtgggtgtc ttagttactg    4200
ccattgctat gagggacacc ataagtaaag caacttataa cagaaagcat ctaattgggg    4260
gcttgcttac agtttcagag tgttggtcca tttctactac gatgtcaggc aggcatggcg    4320
ctggagcaga acagaagctg agagcaccca tctagatctg caagttgcag gtttagaaag    4380
agaacacgac tgggcctggt gtgtgctttc aaaaccttaa attccacctc cagtgctccg    4440
cctcttaacc ctgcctaaac agtccacaaa ctggaaccaa accttcaaa tatgggagcc    4500 tctgagggaa cattctcatt taaaccagca cagtgggaat ctcaggatgg aggtgtaggg    4560
cttaggggaa ggcaggtctc tagggactgt ggagtatggg gaacactgga gtggagggg    4620 gttgctcctg gaggacggat ctgttaggat gaggcccagg agtgggaaag tctagggtgt    4680
ggctttgtac agaaccaggg aactagaggc agtcatgtta gatgccaagg ggctcctgtc    4740
ccagttggtt tccgctctct gtcccccact aggtggtgaa gtaccctta cacgccatca    4800 tggagatcaa agagtacctg attgacgtag cctccaaggc cggcatgcac tggctctcca    4860
ccattgtacc cacccatcac atcaacgccc tcatcttctt cttcatcatc agcaacctaa    4920
ccatcgactt cttcgccttc ttcatcccc tggtggtctt ctatctgtcc tttgtgtcca    4980
tggtcatctg cacgctcaag gtgttccagg acagcaaggc ctgggagaac ttccgtactc    5040
tcaccgacct gctgctgcgc ttcgagccca acctagacgt ggagcaggcc gaagtgaact    5100
tcggctggaa ccacctggag ccctacatcc acttcctact gtcagtcgtc tttgtcatct    5160
tctccttccc gctggccagc aaggactgca tccctgctc ggagctggcc gtcatctcca    5220
ccttcttcac ggtgaccagc tacatgagcc tgagcagctc tgctgagccc tataccaggc    5280
gtgccctggt caccgaggtg gctgccggct tgctgtccct tctgcccacc gtgcctgtgg    5340
actggcgctt cctgaaagta tcggccaga cttttcttcac tgtgcccgtt ggccacttca    5400
tcatcctcaa cgtcagcctc ccctgcctgc tctatgtcta tctctttttac ctcttcttcc    5460 gcatggccca gctgaggaac ttcaagggca cttattgcta cctggtgccc tacctggtgt    5520
```

```
gcttcatgtg gtgtgaactg tccgtggtca tcctgctcca gtctaccggc ctgggcttgg    5580
tccgggcctc catcggctac ttcctcttcc tctttgccct ccccatcctg gtggctggcc    5640
tcgccttgat gggcacggtg cagtttgccc gatggttcct gtcgctggac ctcaccaaga    5700
tcatggtcac cacggtgatc tgcggcgtac ccctgctttt ccgttggtgg accaaggcca    5760
acttctcagt gatggggatg gtcaagtccc tgacgaagag ctccatggtg aagctcattc    5820
tggtgtggct aacggccatc ctgctcttct gctggttcta cgtgtaccgc tcagaaggca    5880
tgaaggtcta caactccaca ctcacctggc agcaatatgg cttcctatgt gggccccggg    5940
cctggaagga aactaacatg gcccggaccc agatcctgtg cagccacctg gagggccaca    6000
gggtcacgtg gacaggccgc ttcaagtatg tccgagtgac cgagatcgac aacagtgctg    6060
agtcggccat caacatgctc ccgttcttcc tgggcgattg gatgcgctgc ctgtatggcg    6120
aggcctaccc atcttgtagc tctggtaaca cgtccacggc agaggaggag ctctgccgtc    6180
tcaagcagct ggccaagcac ccctgccaca tcaagaagtt tgaccgctac aaatttgaga    6240
tcacagtggg catgcccttt ggcaccaacg gcaaccgcgg ccatgaagag gacgacatca    6300
ccaaggacat tgttctccgt gccagcagcg agttcaagga cgtgctgctg aacctgcgcc    6360
aggggagcct catagagttc agcaccatcc tcgagggccg cctgggtagc aagtggcccg    6420
tcttcgagct caaggccatc agctgcctca actgcatgac gcagctgtca cctgcccgga    6480
ggcacgtgaa gatcgaacag gactggcgta gcacagtgca cggtgccctc aagtttgcct    6540
tcgacttctt cttcttccca ttcctgtctg ccgcctgagg agcgtccgcc gctggaggag    6600
gcttcggtgc atgttgctgt gaagtccttc cgtgtggcca cccagccagc tggagcagca    6660
ctgtgccgtg tgtgtgtgtg tgtgtgtgtg tgtgtgtgtg tgtgtgtgtg tgtgtgtgtg    6720
tgtgtgtgtg tgtgtgtatg tgtattctgc tctcatgtgg ttagatccca ggctctctgc    6780
tcacctgtag atcgcagatc ctgctggagg gtggttctct ttagcactgt ccactttgaa    6840
tgccgagtgt cataagaaat tgcatgctat cttcactcac aatcctgccc ttccctcaca    6900
gagctggaac tccaagcctg ccccaaaga ccctccgtca cgaagagcac tttacagata    6960
agaatcttcc tttccagttc ttcatgcctc cttcctgccc tttccttact ttgtgttgga    7020 tttcttttc gaagawccaa atatgtgtgt atgtagactt catggtagtg tttcttattt    7080
atttggttgc tgctaagcct tgacagtggt tcaccttcct gggctgttcc cagtggtcac    7140
gtcctgcctg gcttcctact tgggtatagc atgtccaaac tgggctctga acactacagc    7200
ctgccttgga gctggcctat ctctggggt gttagagagt ttgtggggat ctcttctgag    7260
taccccagga cttgggaaat aatgcaagag tatccctttc agtacatagg taagcttggc    7320
tatgttcaat atggcagagc caaaagccaa gttctaaggc agccgaaata aaaagctttg    7380
aaacctatag ccttgccttc tggtttgatt acagggagcc ttgtctggtt gtgtgtgtgt    7440
gtgtgtgtat gtgtgtgtgt gtgtgtgtgt gtgtgtgtgt gtgtgtgtgt gtgtgtgttc    7500
acacgcgcgc tcgagcaaca tagtatgtat gaacccagat tcagtgaaaa tgtgccagtt    7560
gggtgactga ggatagaact gatatcccgc acagttgaca ccatctgcta tatagctgat    7620
tggcaccatc caggtgtgag ggtccccgag gtcgcagcag taacagcaca tggctgttga    7680
ccctggcctt ggggtgaaaa gtgctttctt tgtgtcgagg atcactgaaa cccaggtcac    7740
caattgggtc gtctgcatga gtcacagtct ggggtttgtg ctgctctctt cagtcacgtg    7800
tggtaattcc acacgggcat aatcagggtt tgtcatgggg actggaagag ttatggtgct    7860
gggccggttt catccctgtt actgtggcaa acaccatgac caaaatcaac ttaggggagg    7920
```

```
aaagggtga cttggcttgt atttgtcggc catagttcat cactgaggag aggcagggca    7980
ggaactcaag gccagcctgc ttggtattcc tcactcactg ccaaggaagt acagcaggga    8040
cttgctggct cactctatgg ctcactcaaa gagccatgct tagctaactt tcttatacag    8100
cccagcaccg cctgcctagg gaatggaatt gcccaacatg ggccaagcct cctacatcta    8160
ttaacagggt aaaccccatg cacaagccca cagaccactc tgatctgggc acttgctcca    8220
ttgacactcc cttctcaggt gacacaagcc tgtgttaaag ctaactggga caggctctgt    8280
gtgggcgagt acccctctgc agtggttttgt tttatttaag ttaatagggt ctcacggtgt    8340
atggagctca ggatggtctg aaatccactg tgtagcctag cctggcctcg aacttggtga    8400
tcctgctatc tcaaacctct caagtcctga gattacaggg ctgagcctcc aagctgccat    8460
ttggtttctg tcctgaaggt gaggactgcc tgactctatg agagggatga aaaagagag    8520 atctggtacg tgtagacagg cctttcctgc tggtgttgaa gaatgtcatg tggagtattc    8580
atcacctaac ctgggctgac attaacggtt gtggctgcct ccattttcct cggggtcact    8640
cacctgggac actggaatgg tagcagcttc atcctcttac cccatgggtc tgcctcaaac    8700
tccacatgtt aaagggatat tcagggccca taagtacatg catttgctct tgggggtctt    8760
ctccagcagt gggtgtggcc agctgtccag tatcacccct ctccccatcc tccaccacaa    8820
ggccacacca cgtagtcatc atgccactga ttgtgtggga cctttggagc aaatcacaga    8880
tgaccttcta cctatccttg ccttgattgg gggggggggg ggtgtgtccg tgacaacgcc    8940
atctacagaa gacactaggt tcagagagca ggatgggact gatacaggcc tgtccccagg    9000
ccaccacact gctgccatca cctcatgaca tctcccctgg gaatgaagca gactcaggga    9060
gaaccccaag cagtcatgga ttctgggtgc cacttctcat tctaacttga actcctatgt    9120
gcccaagagc cttgtgatgg cagctaaccc caacttccat gactctagct ggaacaacat    9180
ttctcagagc ttccacgcaa tgagccatgt gcaaaaatcc catagagtgc ctggagtgta    9240
gtagaagcat tgctctccag tctggaagca gcctttccag ccgatgggca gctgctgagc    9300
ctcatgcctg ctccctccca gtgctctaat cttgagtaag gtccctcagc atcagcctca    9360
tcagctgttc tgagagagag aagggttgat tgtctgggaa ggtagtcaca agacattgat    9420
aagccttcca caaacttggg tcttctttca acattcctg aacattgaaa ccttgggcca    9480
caggcactgt gacgtccttg ccggtttcgt aagtatttca aacagaaaac agcaatgttt    9540
agattagagc tgagctaaat gactggatct aaacagggcc tggcgtctcc tggctgactg    9600
tacagcactc taacacgcaa gctgccctcc ttcctcctag ccatctgacc acaaccattt    9660
ggccggtatc tgtgacttac tgtttgaaat attccttata gatattagct aggagcctgg    9720
atgctttcca tgcaaccagt agggacacct gagtctaggt ggcagggttc ctggtctcta    9780
gatcttgccc tttccactct aaaacttctc tggaggcagc ctggcatcct tggaagtggg    9840
tgtacattag ggagaggcct tcccctaaa ggtcctgacc cccagggca gcctaaggcc    9900 ctccagccaa tgcagagtct ctctcctagg ccccctcct cccaggcaga tctgggttgg    9960
gggtgtagca tccttacaca gacctgagac ctgcacagcc ctggcccaac tgccctgcct   10020
gcagaccaga taccacatcc acaggctgga tccattgttg agctgtggct gtcgtcagaa   10080
tgctcactct tggtccagaa gctctgtccc aagggtcagc tattatccga gttgttgagg   10140
cagaacctga gtcctacaag ccctcactat tcaggcctttc cctcctcctg ccctcactat   10200
acagacctgc ccttccccta ccccccacaat aggccaacta aacacatgaa gaacagtgaa   10260
```

-continued

```
aagcagagaa aggagattat tttatggggc catatcggaa agagaaacaa gatttcaagt   10320
aacattcttc cccaagtcct gcgaggacag aggttctcaa cctgtggggc acaaccccnt   10380
tggggtttga atgactttc acagggttg cttgccaaag accatcagaa aacacaggta     10440
tttacattcc aattcatgac agtagtaaaa ttacagttat gcagtagcaa tgaaaataat   10500
tttatggttg gggtgaccac atcatgaaga actgtattaa agggtcccag cattaccact   10560
gctctatggt acttgggatt taaatagaga dacagctatg cacaaggcgt gtcaaggtgt   10620
ggtcccactc actgactcaa ctccagtccc tctcacaagg tgattgccaa gttgtcagaa   10680
tttgtaaaag tctttctaga aagaagctct ctctctctct ctctctctct ctctctctct   10740
ctctctctct ctctctctct mtmwmwctcw cwcycycaga gagagagaga gagagagaga   10800
gagtgttttt tatatatata tatatatata tacacacact ctctctctct ctctctctct   10860
ctctctctct cnananaggg ggggggggg gccacacaca cacacacata tatatat       10917
```

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 2
gcccgggccc ggctcaat                                                 18

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 3
ttcttcccgg ctgccggttt ga                                            22

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 4
atctgcggcg taccctgct tttc                                           24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 5
gtccgggcca tgttagtttc cttc                                          24

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 6

```
gtcaagcttc tgactcatca tgttaactcc cgagtgcagc c                          41

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 7
agctcctcgc ccttgctcac taaagggtac ttcaccac                              38

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 8
gtggtgaagt acccctttagt gagcaagggc gaggagct                             38

<210> SEQ ID NO 9
<211> LENGTH: 96
<212> TYPE: DNA
<213> ORGANISM: Artificial Sequence
<220> FEATURE:
<223> OTHER INFORMATION: Description of Artificial Sequence: primer

<400> SEQUENCE: 9
gagtgaattc ctcgagggaa gttcctattc ggaagttcct attcttctag aagtatagga     60
acttcagttt ggacaaacca caactagaat gcagtg                                96

<210> SEQ ID NO 10
<211> LENGTH: 90
<212> TYPE: DNA
<213> ORGANISM: Artificial Sequence
<220> FEATURE:
<223> OTHER INFORMATION: Description of Artificial Sequence: primer

<400> SEQUENCE: 10
gctggtacca tcgatgaagt tcctatactt ctagaagaat aggaacttcc gaataggaac     60
ttccaacata gtatgtatga acccagattc                                       90

<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence: primer

<400> SEQUENCE: 11
gttgcaagct tcccgggctg acaacttggc aatcaccttg tgag                       44

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 12
gcgcatgctc cagactgcct tg                                               22
```

```
<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 13
ctgacaactt ggcaatcacc ttgtgag                                        27
```

MICE HETEROZYGOUS FOR WFS1 GENE AS MOUSE MODELS FOR DEPRESSION

The present application is a continuation of U.S. application Ser. No. 09/871,107, filed May 31, 2001, now abandoned, which claims priority under 35. U.S.C. §119(e) from U.S. Provisional Patent application No. 60/209,394 filed Jun. 1, 2000. Applicants herewith incorporate the entire text of that application by reference.

FIELD OF THE INVENTION

The present invention relates generally to the field of molecular biology. More particularly, the present invention relates to transgenic nonhuman animals that may serve as models for depression.

BACKGROUND OF THE INVENTION

Transgenic animals are a valued tool in the arsenal of techniques employed in the elucidation of human disorders as well as in the characterization of the in vivo effects of a given therapeutic regimen. Such animals are characterized by the presence of a new or altered exogenous DNA integrated into their genome; usually to introduce a foreign gene and/or "knock out" an endogenous gene. To date, there are no known genetic or transgenic models for depression.

Major depression represents one of the most common mental illnesses, affecting between 5–10% of the population. The disease is characterized by extreme changes in mood which may also be associated with psychoses. Depression comes in varied forms and is an extremely difficult disorder to treat. Patients are often reluctant to seek the medical attention necessary to diagnose the disorder. Furthermore, even if patients do seek psychiatric help, psychoanalytic approaches alone are often ineffective at providing amelioration for the disorder.

Clinically, depression may be classified into depressive disorder, dysthymic disorder and depressive disorder not otherwise specified. Major depressive disorder and dysthymic disorder are differentiated based on chronicity, severity and persistence. In major depression, the mood must be present for two weeks. In dysthymic disorder, the depressed mood must be present most days over a period of two years. Usually major depressive disorder is characterized by its sharp contrast to normal functioning. A person with major depressive episode can be functioning normally and feeling fine and suddenly develops severe symptoms of depression. By contrast, a person with dysthymic disorder has chronic depression with less severe symptoms than major depression.

Numerous drugs have been developed to treat depression including for example serotonin re-uptake inhibitors (SSRI), such as sertraline (registered trademark ZOLOFT, Pfizer), fluoxetine (PROZAC—Eli Lilly), paroxetine (PAXIL—Smith Kline Beecham) and fluvoxamine (LWOX); tricyclic antidepressants such as ELAVIL (Merck, Sharpe and Dohme), aminoketone antidepressants such as bupropion, and lithium, a metal used to treat bipolar disorder. However, these drugs are very potent, often generating problematic side effects such as lethargy, clouded thinking and a lack of ability to concentrate. Further, the road to development of such drugs is long and expensive and hindered by the lack of availability of suitable animal models on which new antidepressant drugs can be tested.

Insights into the monitoring and management of depressive disorders are needed in order to provide more effective treatment for the complex array of disorders that fall under the term "depression". However, the precise identification of models which may be employed to study such disorders remains elusive. In order to develop pharmacologic strategies for treatment of depression in humans, it will be important to establish animal models which accurately reflect the pathological profile of the disorders.

SUMMARY OF THE INVENTION

The present invention provides a non-human transgenic mammal selected from the group consisting of a transgenic mammal comprising a genome containing a single copy of a wild-type WFS1 gene wherein the genome has been modified to contain a WFS1 null allele; and a transgenic progeny of the transgenic mammal that comprises a genome containing a single copy of a wild-type WFS1 gene and a WFS1 null allele. In preferred embodiments, the mammal exhibits chronic stress-induced neurochemical changes associated with depression and/or increased behavioral traits associated with depression as compared to a similar mammal comprising a homozygous wild-type WFS1 genotype. More particularly, the increased behavioral traits are measurable in behavioral assay to monitor depression. In specific embodiments, the assays contemplated for such measurements include but are not limited to swimming time in a Porsolt assay, immobility in the tail suspension assay, measurements of learned helplessness such as failure to escape avoidable shock and measures of anhedonia which is reflected as a loss of responsivity to rewards. Of course these are merely exemplary assays and those of skill in the art will be aware of other behavioral assays that may be substituted for these assays and still yield appropriate indications of depression in accordance with the present invention.

In certain embodiments, it is contemplated that the administration of at least one antidepressant selected from the group consisting of a serotonin-selective re-uptake inhibitor; norepinephrine re-uptake inhibitor; tricyclic antidepressant; and monoamine oxidase inhibitor to said mammal correlates with an improved performance in a forced swim assay (a Porsolt assay), a tail suspension assay, learned helplessness assay, a responsivity to reward assay and an assay that monitors chronic stress-induced neurochemical changes. In some embodiments, the administration of at least one antidepressant selected from the group consisting of a serotonin-selective re-uptake inhibitor; norepinephrine re-uptake inhibitor; tricyclic antidepressant; and monoamine oxidase inhibitor to said mammal correlates with an improved neurochemical levels in said mammal as determined by an assay that monitors chronic stress-induced neurochemical changes.

In particular aspects, the null allele lacks a nucleotide sequence encoding a transmembrane domain of the wild-type WFS1 protein. In one variation, the null allele lacks a nucleotide sequence encoding all transmembrane domains of the wild-type WFS1 protein. In other embodiments, the null allele comprises a mutation in exon 8 of wild-type WFS1-encoding gene. Exemplary mutations include but are not limited to a deletion mutation, an insertion mutation, a non-sense mutation or a missense mutation. In certain examples, the mutation results in a disruption of expression of all or part of exon 8 of wild-type WFS1-encoding gene. In other examples, the mutation is a deletion of all or part of exon 8 of wild-type WFS1-encoding gene. In preferred embodiments, the mammal is a rodent such as a mouse. A highly preferred mouse is a mouse of the C57BL/6J strain or a mouse having the substantial characteristics of a C57BL/6J strain. In certain embodiments, knockouts are created by homologous recombination in ES cells from a 129sv mouse strain and back crossed against C57BL/6 strain. In other embodiments, the knockouts are created in ES cells from C57BL/6 mice and implanted into pseudo-pregnant mice for gestation. The wild-type WFS1 gene may be a mouse WFS1 gene, alternatively the wild-type WFS1 encoding gene is a human WFS1 gene. In exemplary embodiments, the wild-type WFS1 encoding gene has the sequence of SEQ ID NO:1.

In an exemplary transgenic mammal, the null allele comprises a chimeric gene in which WFS1 exon 8 has been replaced by a nucleic acid sequence encoding a marker. Preferably, the marker is selected from the group consisting of green fluorescent protein (GFP), β-galactosidase, luciferase, FLAG, HA and His6.

Other aspects of the present invention provide a method of making a non-human transgenic mammal comprising preparing a construct for transforming a mammalian cell, said construct comprising a polynucleotide sequence sufficiently homologous with a WFS1 gene in a mammalian cell to recombine with said WFS1 gene, introducing the construct into mammalian embryonic stem cells; selecting a cell which has incorporated into its genome said polynucleotide in a WFS1 locus in a manner that disrupts the wild-type function of said WFS1 gene at said locus; introducing said selected cell into a blastocyst; implanting said blastocyst into a host animal to produce a chimera wherein said chimeric mammal comprises stably incorporated into its genome a disruption in the WFS1 gene; breeding said chimeric mammal to produce a transgenic mammal that is heterozygous for said disruption in said WFS1 gene. As used above, the term "sufficiently homologous" is intended to mean that the sequence is such that it allows homologous recombination to occur.

The invention further provides a method of screening for an antidepressant agent comprising administering a composition comprising a candidate antidepressant substance to a mammal having a heterozygous WFS1 genotype, and comparing the behavior of said mammal receiving said candidate antidepressant substance with the behavior of a mammal having a heterozygous WFS1 genotype that has not received said candidate antidepressant substance, wherein a change the behavior characteristics related to depression of the mammal receiving the candidate antidepressant substance as compared to the mammal not receiving the test substance is indicative of said candidate antidepressant substance being an antidepressant. In specific embodiments, the mammal is a non-human transgenic mammal selected from the group consisting of a transgenic mammal comprising a genome containing a single copy of a wild-type WFS1 gene wherein the genome has been modified to contain a WFS1 null allele; and a transgenic progeny of the transgenic mammal that comprises a genome containing a single copy of a wild-type WFS1 gene and a WFS1 null allele. Preferably, the mammal is a mouse and the monitoring comprises monitoring the response of said mammal to chronic stress or the behavior of said mammal in measurements of stress avoidance behavior or reward-seeking behavior.

The invention also provides a method of screening for an antidepressant agent comprising administering a composition comprising a candidate antidepressant substance to a mammal having a heterozygous WFS1 genotype, and comparing characteristics related to the mechanism of action of known antidepressants of said mammal receiving said candidate antidepressant substance with such characteristics of a mammal having a heterozygous WFS1 genotype that has not received said candidate antidepressant substance, wherein a change in characteristics related to the mechanism of action of known antidepressants of the mammal receiving the candidate antidepressant substance as compared to the mammal not receiving the test substance is indicative of said candidate antidepressant substance being an antidepressant. Preferably, the characteristics related to the mechanism of action of known antidepressants are neurochemical changes associated with chronic depression.

The foregoing methods of the invention will identify novel antidepressant agents which can be formulated into pharmaceutical compositions suitable for administration to a human or other mammalian subject suffering from depression. Thus, for any of the screening methods described herein, an additional step of manufacturing a composition comprising the identified antidepressant is contemplated. Preferred compositions comprise the antidepressant compound, substantially purified, in a pharmaceutically acceptable carrier.

Other aspects of the invention provide an antidepressant identified according to any of the screening methods of the invention. For example, the invention provides an antidepressant compound identified according to a method of screening for an antidepressant agent comprising administering a composition comprising a candidate antidepressant substance to a mammal having a heterozygous WFS1 genotype, and comparing characteristics related to the mechanism of action of known antidepressants of said mammal receiving said candidate antidepressant substance with such characteristics of a mammal having a heterozygous WFS1 genotype that has not received said candidate antidepressant substance, wherein a change in characteristics related to the mechanism of action of known antidepressants of the mammal receiving the candidate antidepressant substance as compared to the mammal not receiving the test substance is indicative of said candidate antidepressant substance being an antidepressant.

Other aspects of the invention provide an antidepressant identified according to a method of screening for an antidepressant agent comprising administering a composition comprising a candidate antidepressant substance to a mammal having a heterozygous WFS1 genotype, and comparing the behavior of said mammal receiving said candidate antidepressant substance with the behavior of a mammal having a heterozygous WFS1 genotype that has not received said candidate antidepressant substance, wherein a change the behavior characteristics related to depression of the mammal receiving the candidate antidepressant substance as compared to the mammal not receiving the test substance is indicative of said candidate antidepressant substance being an antidepressant. In specific embodiments, the mammal is a non-human transgenic mammal selected from the group consisting of a transgenic mammal comprising a genome containing a single copy of a wild-type WFS1 gene wherein the genome has been modified to contain a WFS1 null allele; and a transgenic progeny of the transgenic mammal that comprises a genome containing a single copy of a wild-type WFS1 gene and a WFS1 null allele.

Another aspect of the present invention provides methods of treating a mammal comprising administering to the mammal an antidepressant, identified according to the methods described herein, in an amount effective to alleviate the symptoms of depression. In certain embodiments, the method further comprises additional therapeutic intervention wherein said intervention is chemical intervention with a known antidepressant.

The invention also contemplates a colony of laboratory animals wherein said animals are useful in screening for antidepressant substances, said colony including members heterozygous for a mutant mammalian WFS1 gene. In particular embodiments, the colony further comprises members homozygous for a mutant WFS1 gene. In other preferred embodiments, the colony further comprises animals having a wild-type WFS1 expression. In still other embodiments, the colony consists of mammals comprising a WFS1 heterozygous genotype. Such animals are readily identified through standard genetic testing of litters containing homozygotes and heterozygotes and a colony consisting solely of heterozygotes represents one preferred colony for screening compounds of potential antidepressant therapeutic value.

Other aspects, features and advantages of the present invention will be apparent from the drawings and detailed description. It should be understood that the detailed description presented below, while providing preferred embodiments of the invention, is intended to be illustrative only since changes and modification within the scope of the invention will be possible whilst still providing an embodiment that is within the spirit of the invention as a whole.

DETAILED DESCRIPTION OF THE PREFERRED EMBODIMENTS

Figure 1:
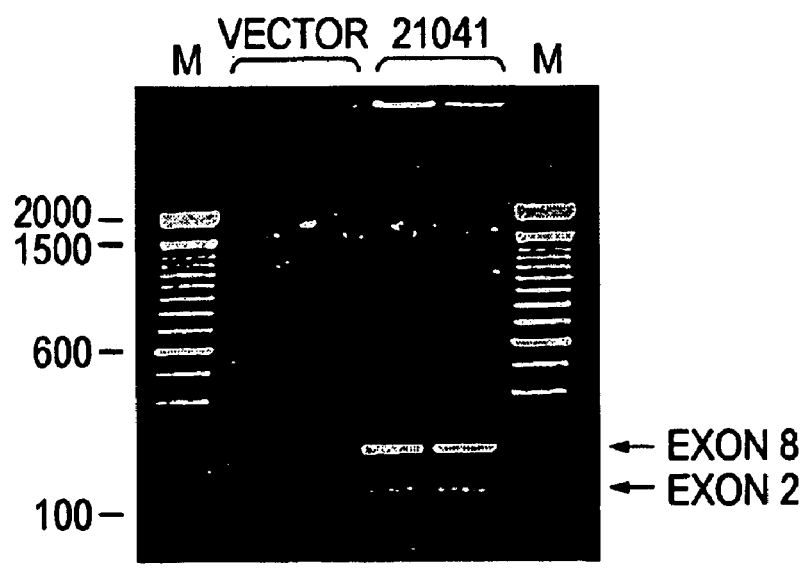
FIG. 1. Shows the mouse WFS1 genomic DNA clone which contains at least exons 2 and 8. Primers corresponding to exons 2 and 8 were used in PCR with either clone 21041 or the corresponding vector alone as template. Products of the expected sizes were amplified from clone 21041 but not from the vector alone. M, molecular mass standards, with size in basepairs listed on the left.

Depression is a major disorder in the United States affecting between 5–10% of the population. There are presently no models that can predict the progression of the disorder of the efficacy of a given pharmaceutical intervention.

The present invention addresses this need by providing a transgenic nonhuman animal that is a model for depression in humans. Such an animal may be used to monitor the efficacy of a drug against depression. The animal is preferably a knockout mouse that is heterozygous for a disruptive mutation in the WFS1 locus associated with Wolfram's syndrome. Methods and compositions for making and using the animal are disclosed herein below.

I. Wolfram's Syndrome and Wolframin

Wolfram Syndrome (WFS) is an autosomal recessive disorder most frequently characterized by diabetes insipidous, diabetes mellitus, optic atrophy and deafness (Strom et al., *Hum. Mol. Genetics.* 7(13) 2021, 1998). Minimally, individuals presenting this syndrome have diabetes mellitus and optic atrophy, however, diabetes insipidous sensorineuronal deafness, urinary tract atony, ataxia, peripheral neuropathy, mental retardation and psychiatric illness also are observed in the vast majority of patients. A range of psychiatric conditions also have been associated with WFS, including dementia, psychosis, affective disorder, suicide and assaultive behavior. (Owen, *Mol. Psychiatry,* 3, 12, 1998; Swift et al., *Am. J. Psychiatry,* 148, 775, 1991).

Recently, WFS was linked to markers on chromosome 4p. On the basis of meiotic recombinant and disease associated halotypes, the WFS gene was identified as wolframin (WFS1). This gene codes for a predicted transmembrane protein which is expressed in a variety of tissues including the brain and pancreas. Loss of function mutations in both alleles of this gene are associated with the diseased characteristics of WFS (Inoue et al., *Nature Genetics* 20, 121, 1998; Strom et al., *Hum. Mol. Genetics.* 7(13) 2021, 1998).

While the homozygous loss of function mutations in the WFS1 gene have been associated with WFS, individuals that are blood relatives of individuals manifesting WFS have a greater predisposition to psychiatric illness than those individuals that are not genetically related to individuals suffering for WFS. (Swift et al., *Mol. Psychiatry,* 3, 86–91, 1998).

The present invention is directed to the production and use of transgenic animals that are heterozygous for a WFS1 mutation. The human transmembrane protein was described in 1998 (Strom et al., *Hum. Mol. Genetics,* 7(13) 2021–2028). The 890 amino acid protein corresponds to a predicted molecular weight of 100 kDa.

The wildtype WFS1 protein is expressed primarily in heart, pancreatic islet cells, placenta, lung and brain with lower levels being found kidney, skeletal muscle and liver.

Individuals that are homozygous for mutations in wolframin have WFS. The mutations may include stop, frameshift, deletion, insertion, missense and nonsense mutations. In the present invention, cells heterozygous for WFS1 mutations are generated and are employed for generating transgenic non-human animals.

The transgenic animals, preferably mice, that are heterozygous for mutations that provide a predisposition for WFS develop symptoms that mimic human depressive disorders. Thus, these mice will be useful for identifying drugs and genes that may be employed to ameliorate depression. In specific embodiments, the mutations in the WFS1 gene employed herein produce a protein that lacks all or some of the predicted nine to twelve transmembrane domains of wolframin. Thus in certain embodiments, it is contemplated that 1, 2, 3, 4, 5, 6, 7, 8, 9, 10, 11 or 12 of the transmembrane regions have been either deleted or mutated in such a way as to disrupt the normal function of the wolframin. However, the invention may be practiced by the introduction of any WFS1 mutation that substantially eliminates WFS1 function. Exemplary mutations include any mutations in WFS1 correlated with WFS in humans.

II. Methods of Knocking Out the WFS1 Gene

The transgenic animals of the present invention are constructed using an expression cassette employed to insert mutations in a WFS gene of the animals, or to replace WFS1 genes with orthologs, such as human wild-type and mutant alleles that correlate with WFS. In preferred embodiments, the resulting mutation blocks the expression of the WFS1 gene in the transgenic animal. The present section describes various methods of knocking out the expression of WFS1 gene. Section III below details the components of the expression cassettes used in the present invention.

Four basic approaches are contemplated for blocking expression of the WFS1 gene. First, constructs may be designed to homologously recombine into particular endogenous gene loci, rendering the endogenous gene nonfunctional. Second, constructs are designed to integrate randomly throughout the genome. Third, constructs are designed to introduce nucleic acids complementary to a target endogenous gene. Expression of RNAs corresponding to these complementary nucleic acids will interfere with the transcription and/or translation of the target sequences. And fourth, constructs are designed to introduce nucleic acids encoding ribozymes—RNA-cleaving enzymes—that will specifically cleave a target mRNA corresponding to the endogenous gene. While homologous recombination is the preferred method, it is contemplated that the other strategies also may be useful for blocking WFS1 gene expression.

A. Homologous Recombination

A desirable approach for blocking of endogenous WFS1 protein production involves the use of homologous recombination. Homologous recombination relies, much like antisense described below, on the tendency of nucleic acids to base pair with complementary sequences. In this instance, the base pairing serves to facilitate the interaction of two separate nucleic acid molecules so that strand breakage and repair can take place. In other words, the "homologous" aspect of the method relies on sequence homology to bring two complementary sequences into close proximity, while the "recombination" aspect provides for one complementary sequence to replace the other by virtue of the breaking of certain bonds and the formation of others.

Put into practice, homologous recombination is used as follows. First, a target gene is selected within the host cell. Sequences homologous to the target gene are then included in a genetic construct, along with some mutation that will render the target gene inactive (stop codon, interruption, etc.). The homologous sequences on either side of the inactivating mutation are said to "flank" the mutation. Flanking, in this context, simply means that target homologous sequences are located both upstream (5') and downstream (3') of the mutation. These sequences should correspond to some sequences upstream and downstream of the target gene. The construct is then introduced into the cell, thus permitting recombination between the cellular sequences and the construct.

As a practical matter, the genetic construct will normally be designed to act as far more than a vehicle to interrupt the gene. For example, it is important to be able to select for recombinants and, therefore, it is common to include within the construct a selectable marker gene. This gene permits selection of cells that have integrated the construct into their genomic DNA by conferring resistance to various biostatic and biocidal drugs. In addition, a heterologous gene that is to be expressed in the cell also may advantageously be included within the construct. The arrangement might be as follows:

. . . vector . . . 5'-flanking sequence . . . heterologous gene . . . selectable marker gene . . . flanking sequence-3' . . . vector . . .

Thus, using this kind of construct, it is possible, in a single recombinatorial event, to (i) "knock out" an endogenous gene, (ii) provide a selectable marker for identifying such an event and (iii) introduce a heterologous gene for expression. In the present invention, a preferred embodiment involves knocking out the endogenous mouse WFS1 gene and replacing it with normal or mutant forms heterologous WFS1 gene. Most preferably, normal or mutant forms of human WFS1 are introduced into homozygous mice null for mouse WFS1. Of course, it is contemplated that the transgenic mice may be generated using heterologous WFS1 from other organisms including but not limited to mammals such as sheep, cows, pigs, horses, rats, dogs cats, as well as other primates such as monkeys, apes, and baboons.

Another refinement of the homologous recombination approach involves the use of a "negative" selectable marker. This marker, unlike the selectable marker, causes death of cells which express the marker. Thus, it is used to identify undesirable recombination events. When seeking to select homologous recombinants using a selectable marker, it is difficult in the initial screening step to identify proper homologous recombinants from recombinants generated from random, non-sequence specific events. These recombinants also may contain the selectable marker gene and may express the heterologous protein of interest, but will, in all likelihood, not have the desired "knock out" phenotype. By attaching a negative selectable marker to the construct, but outside of the flanking regions, one can select against many random recombination events that will incorporate the negative selectable marker. Homologous recombination will likely not introduce the negative selectable marker, as it is outside of the flanking sequences.

In a first embodiment, a target WFS1 gene within a host cell is selected as the target gene into which a selected gene is to be transferred. Sequences homologous to the target gene are included in the expression vector, and the selected gene is inserted into the vector such that target gene homologous sequences are interrupted by the selected gene or, put another way, the target gene homologous sequences "flank" the selected gene. In preferred embodiments, a drug selectable marker gene also is inserted into the target gene homologous sequences. Given this possibility, it should be apparent that the term "flank" is used broadly herein, namely, as describing target homologous sequences that are both upstream (5') and downstream (3') of the selected gene and/or the drug selectable marker gene. In effect, the flanking sequences need not directly abut the genes they "flank." Application of a drug to such cells will permit isolation of recombinants.

On the other hand, site-specific recombination, relying on the homology between the vector and the target WFS1 gene, will result in incorporation of drug selectable marker or other gene to replace the wild-type WFS1 gene. Further screens for these phenotypes, either functional or immunologic, may be applied.

The Cre/Lox site specific recombination system from bacteriophage P1 (Sauer, *Methods Enzymol.*, 225:890–900, 1993; Sauer, *Methods*, 14(4) 381–392, 1998, available through Gibco/BRL, Inc., Gaithersburg, Md.) may be used to remove specific genes out of a genome. Briefly, the system involves the use of a bacterial nucleotide sequence known as a LoxP site, which is recognized by the bacterial Cre protein. The Cre protein catalyzes a site specific recombination event. This event is bidirectional, i.e., Cre will catalyze the insertion of sequences at a LoxP site or excise sequences that lie between two LoxP sites.

Thus, if a construct containing a WFS1 gene also has LoxP sites flanking the WFS1 gene, introduction of the Cre protein, or a polynucleotide encoding the Cre protein, into the cell will catalyze the removal of the WFS1 gene. In a further engineering step, it will be possible to employ a selectable marker to be inserted into the LoxP site vacated by the WFS1 gene. This technique will thus yield a cell which is null for the WFS1 phenotype that can be recognized by the expression of the selectable marker phenotype. This technology is explained in detail in U.S. Pat. No. 4,959,317, which is hereby incorporated by reference in its entirety. The various markers that may be employed are well known to those of skill in the art and certain examples are described in further detail elsewhere in the application.

Yet another system that may be used for homologous recombination is the flp/frt recombinase system from yeast. In a preferred embodiment, mouse genomic WFS1 DNA is used to construct a knock-out mouse by homologous recombination. In one such preferred homologous recombination targeting construct, the mouse WFS1 exon 8 is flanked by fit sites. The frt sites are recognized by bacterial flp recombinase, which is capable of removing the DNA between two frt sites (O'Gorman et al., *Science*, 251(4999)

1351–5, 1991; Ludwig et al., *Transgenic Res.*, 5(6) 385–395, 1996; Dymecki, *Proc. Nat'l Acad. Sci.* USA, 93(12), 6191–9196, 1996; Dymecki, *Gene*, 171(2) 197–201, 1996). As such, flp recombinase can be expressed in mouse embryonic stem cells containing the targeting construct and will delete exon 8 before introducing the stem cells into the recipient blastocyst. Methods of introducing the stem cells into the blastocyst are described elsewhere in the specification.

Alternatively, the stem cells containing non-recombinase treated DNA (i.e. intact WFS1 gene) can be used to generate animals with frt sites flanking exon 8 but an otherwise normal WFS1 gene. Crossing these animals with transgenic animals that express flp recombinase under the control of a promiscuous (e.g., actin) or neuronal specific (e.g., CaM kinase II) promoters will delete WFS1 exon 8 in all or selective cells.

Yet another alternative strategy to generating the transgenic animals of the present invention may substitute a selected marker (e.g., green fluorescent protein, GFP) for exon 8. This involves placing such a marker-coding sequence in frame with the first few codons of exon 8. In this manner, the expression of GFP can be employed to select those cells that normally express WFS1. Alternatively, as described above, the GFP could be used to replace the exon 8 and thus be employed to select those cells that express a WFS1 protein lacking the portion encoded by exon 8.

B. Antisense Technology.

In other preferred embodiments, the inventors use antisense oligonucleotides directed to the rat WFS1 gene. Injection of these antisense oligonucleotides into the brains of rats may be an effective method of blocking the expression of the wild-type protein in those animals. Alternatively, the antisense sequences may be delivered through other techniques of gene transfer commonly employed in the art, such as, for example, viral transfer, receptor-mediated uptake, liposomal transfer and the like.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation whereas targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo.

Antisense constructs may be designed to bind to the promoter and other control regions, exons, introns or even exon-intron boundaries of a gene. It is contemplated that the most effective antisense constructs may include regions complementary to intron/exon splice junctions. Thus, antisense constructs with complementarity to regions within 50–200 bases of an intron-exon splice junction may be used. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

C. Random Integration.

Although less specific than homologous recombination, there may be situations where random integration will be used as a method of knocking out a particular endogenous gene. Unlike homologous recombination, the recombinatorial event here is completely random, i.e., not reliant upon base-pairing of complementary nucleic acid sequences. Random integration is like homologous recombination, however, in that a gene construct, often containing a heterologous gene encoding a selectable marker, integrates into the target cell genomic DNA via strand breakage and reformation Due to the lack of sequence specificity, the chances of any given recombinant integrating into the target gene are greatly reduced. As a result, it may be necessary to "brute force" the selection process. In other words, it may be necessary to screen hundreds of thousands of drug-resistant recombinants before a desired mutant is found. Screening can be facilitated, for example, by examining recombinants for expression of the selectable marker or even using immunologic or functional tests where the gene inserted to replace the WFS1 gene is not a conventional selectable marker but is some other heterologous gene that may be advantageously incorporated into the genome.

D. Ribozymes.

Ribozymes may be used to block endogenous WFS1 protein production. Ribozymes are RNA-protein complexes that cleave nucleic acids in a site-specific fashion. Ribozymes have specific catalytic domains that possess endonuclease activity (Kim and Cech, *Proc. Nat'l Acad. Sci.* 84(24), 8788–92, 1987; Gerlach et al., *Nature* (London), 328:802–805, 1987; Forster and Symons, *Cell* 49(2):211–20, 1987; Forster and Symons, *Cell* 50(1) 9–16, 1987). For example, a large number of ribozymes accelerate phosphoester transfer reactions with a high degree of specificity, often cleaving only one of several phosphoesters in an oligonucleotide substrate (Cech et al., Cell, 27 (3 Pt 2) p 487–96, 1981; Michel and Westhof, *J. Mol. Biol.*, 216:585–610, 1990; Reinhold-Hurek and Shub, *Nature*, 357:173–176, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence specific cleavage/ligation reactions involving nucleic acids (Joyce, *Nature*, 338:217–244, 1989; Cech et al., *Cell*, 27 (3 Pt 2) p 487–96, 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression (Scanlon et al., *Proc Natl Acad Sci USA.*, 88:10591–10595, 1991; Sarver et al., *Science*, 247:1222–1225, 1990). It has been reported that ribozymes elicited genetic changes in some cell lines to which they are applied; the altered genes included the oncogenes H-ras, c-fos and genes of HIV. Most of this work involved the modification of a target mRNA, based on a specific mutant codon that is cleaved by a specific ribozyme. In light of the information included herein and the knowledge of one of ordinary skill in the art, the preparation and use of ribozymes that are specifically targeted against the WFS1 gene will be useful in abrogating the function of the WFS1 gene product.

III. Expression Constructs for Use in the Production of Transgenic Animals

Exemplary transgenic animals of the present invention are constructed using an expression cassette which includes in the 5'→3' direction of transcription, a transcriptional and translational initiation region associated with expression in the host animal (a promoter region as described below), a DNA encoding a mutant WFS1 gene that when expressed as a protein lacks all or some of the transmembrane regions of WFS1 protein and/or a selectable marker gene, and a transcriptional and translational termination region functional in the host animal. The various regions of such an expression construct are described in further detail in the present section.

The terms "expression vector," "expression construct" or "expression cassette" are used interchangeably throughout this specification and are meant to include any type of genetic construct containing a nucleic acid coding for a gene product in which part or all of the nucleic acid encoding sequence is capable of being transcribed. The transcript may be translated into a protein, but it need not be. Thus, in certain embodiments, expression includes both transcription of a gene and translation of mRNA into a gene product. In other embodiments, expression only includes transcription of the nucleic acid of interest (e.g., where the nucleic acid is an antisense of the gene of interest).

A. Mutant WFS1 Transgene.

The transgenic animals of the present invention are produced with transgenes which comprise a coding region that encodes a gene product which lacks all or a portion of the transmembrane region of wild-type wolframin.

Coding regions for use in constructing the transgenic mice include mouse, human and rat wolframin genes. The coding regions may encode a substantially complete polypeptide, or a fragment thereof, as long as one or more transmembrane regions is deleted or WFS1 is otherwise modified to cause loss of its function. The coding regions for use in constructing the transgenes of the present invention further may include mutations that may be generated through frameshifts, stop mutations, substitution mutations, insertions mutations, deletion mutations, and the like.

In one embodiment of the present invention, there is provided a transgenic animal that expresses a heterozygous mutation in the WFS1 gene. More particularly, the mutation produces a protein that lacks all or part of the WFS1 transmembrane regions. A preferred form of the animal is a mouse that contains a deletion of all or part of exon 8 of the WFS1 gene that normally encodes the wild-type wolframin protein. Most preferably, the WFS1 gene is a human WFS1 gene. For example, in one embodiment, a transgenic mouse contains a wild-type WFS1 gene and a mutant human or murine WFS1 allele. In another embodiment, the mouse contains a murine wild-type WFS1 allele and a mutant allele that includes human WFS1 sequences. Preferred transgenic mice expressing a heterozygous mutation for WFS1 gene will exhibit molecular and pathophysiological responses characteristic of human depression. Of course, it may be useful also to produce mice that are homozygous for the mutation. Such animals will provide useful methods for monitoring and studying WFS and may be useful for breeding heterozygotes in crosses with mice having a homozygous wildtype WFS1 genotype.

In specific embodiments, the inventors identified a P1 clone containing the mouse WFS1 gene and sequenced the 10 kb region of DNA surrounding exon 8. This clone and sequence data were then used to construct a WFS1 knockout mouse using the methods described herein (FIG. 1).

In addition, the inventors identified high throughput genomic sequences from cosmid clones by homology searching of the GenBank htgs database with the human cDNA sequence using the Blast 2.0 algorithm (Altschul et al., "Gapped Blast and PSI-Blast: a new generation of protein database search programs" *Nucleic Acids Research* 25:3389–3402; 1997). These genomic DNA sequences (GenBank accession number AC004689) were consistent with those described by Strom et al., (supra) and Inoue et al., (supra). The inventors further designed oligonucleotides as PCR primers based on the mouse cDNA sequences that would be predicted to be within exons 2 and 8. These exons were chosen because they were large enough to yield large PCR products and because they contained the 5'→3' ends of the translated sequence respectively.

The primers were used to amplify DNA fragments from mouse genomic DNA. Primers within exon 8 were used to screen the SJ129/OLA genomic DNA library in a P1 vector (Genome Systems, St. Louis, Mo.). In preferred embodiments, this screening isolated a clone that contained exon 2 and 8 of the mouse WFS1 gene.

P1 DNA was used as template for walking primer DNA sequencing to extend sequence information in the 5' and 3' directions from exon 8. The initial primers were designed from the mouse WFS1 cDNA (GenBank accession #AJ011971) at regions predicted to be located near the intron 7/exon 8 junction and near the end of the 3' untranslated region. Successive primer walking steps were used to generate a total of 4.78 and 3.54 kb of new mouse genomic sequence data. About 6 kb of this new sequence information was obtained from both DNA strands thereby ensuring greater accuracy of the sequence data.

The sequence of the 5' end of exon 8 was searched against GenBank using BLAST (Atschul, 1990), revealing that the sequence isolated from the primer walking steps included exons 6 and 7 of the mouse gene, thereby indicating that the mouse gene is smaller that the human WFS1 gene. An extrapolation of this technique may reveal that the mouse gene is approximately half the size of the human gene. For the human WFS1 gene, introns 6 and 7 are 3 kb and greater than 6 kb respectively (Strom et al., *Hum. Mol. Genetics.* 7(13) 2021, 1998) however, the mouse introns are 1.47 and 2.88 kb respectively. Exon 8 contains the majority of the WFS1 polypeptide coding region encoding 601 of the 890 amino acid residues and a 0.8 kb 3' untranslated region.

Of the 1.76 kb of exon 8 that was sequenced from clone P1, 1.24 kb comprised the coding region and 0.6 kb comprised the 3' untranslated region. Nevertheless, a comparison of the coding sequences from the mouse WFS1 genomic and cDNA sequences reveals that the coding sequences are identical. The differences in the sequences were found in the 3' untranslated region including an 8 bp deletion in the genomic sequence (cDNA positions 3180–3187), a G→A (position 3381) G→A (3437), C→T (position 3452) G→A (position 3474) and A→G (position 3509). These sequence differences may represent functionally equivalent polymorphic forms, sequencing errors in the published sequence or functionally significant polymorphic forms, for example, affecting stability of the transcript. Regardless, for optimal homologous recombination efficiency it is important that the sequence of the gene used in the construct be identical or nearly so, to the sequence in the embryonic stem cell line being used.

B. Selectable Markers.

In certain aspects of the present invention, the native WFS1 gene is replaced by a selectable marker by using a homologous recombination event. Selectable markers thus perform a two-fold function in the present invention, they are used to replace the wild-type wolframin gene and also are used to detect the stable integration of the transgenic construct into the transgenic animals.

Usually the inclusion of a drug selection marker aids in cloning and in the selection of transformants, for example, neomycin, puromycin, hygromycin, DHFR, zeocin and histidinol. Alternatively, enzymes such as herpes simplex virus thymidine kinase (tk) (eukaryotic), β-galactosidase, luciferase, or chloramphenicol acetyltransferase (CAT) (prokaryotic) may be employed. Immunologic markers also can be employed. For example, epitope tags such as the FLAG system (IBI, New Haven, Conn.), HA and the 6×His system (Qiagen, Chatsworth, Calif.) may be employed. Additionally, glutathione S-transferase (GST) system (Pharmacia, Piscataway, N.J.), or the maltose binding protein system (NEB, Beverley, Mass.) also may be used. The selectable marker employed is not believed to be important, so long as it is capable of being expressed simultaneously with the nucleic acid encoding a gene product. Further examples of selectable markers are well known to one of skill in the art. Particularly preferred selectable markers that may be employed in the present invention are neomycin resistance or a GFP marker.

C. Promoters and Enhancers.

Expression requires that appropriate signals be provided in the vectors. The present section includes a discussion of various regulatory elements, such as enhancers/promoters from both viral and mammalian sources that may be used to drive expression of the genes of interest in host cells. Elements designed to optimize messenger RNA stability and translatability in host cells also are defined. The conditions for the use of a number of dominant drug selection markers for establishing permanent, stable cell clones expressing the products also are provided, as is an element that links expression of the drug selection markers to expression of the mutant phenotype.

In preferred embodiments, the mutant WFS1 nucleic acid or the nucleic acid encoding a selectable marker is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, β-actin, rat insulin promoter, the phosphoglycerol kinase promoter and glyceraldehyde-3-phosphate dehydrogenase promoter, all of which are promoters well known and readily available to those of skill in the art, can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well known properties, the level and pattern of expression of the protein of interest following transfection or transformation can be optimized.

Selection of a promoter that is regulated in response to specific physiologic or synthetic signals can permit inducible expression of the gene product. Several inducible promoter systems are available for production of viral vectors. One such system is the ecdysone system (Invitrogen, Carlsbad, Calif.), which is designed to allow regulated expression of a gene of interest in mammalian cells. It consists of a tightly regulated expression mechanism that allows virtually no basal level expression of the transgene, but over 200-fold inducibility Another useful inducible system is the Tet-Off™ or Tet-On™ system (Clontech, Palo Alto, Calif.) originally developed by Gossen and Bujard (Gossen and Bujard, *Proc Natl Acad Sci USA*. 15;89(12):5547–51, 1992; Gossen et al., *Science,* 268(5218):1766–9, 1995).

In mammalian cells, the CMV immediate early promoter if often used to provide strong transcriptional activation. Modified versions of the CMV promoter that are less potent have also been used when reduced levels of expression of the transgene are desired. Retroviral promoters such as the LTRs from MLV or MMTV are contemplated to be useful in the present invention. Other viral promoters that may be used include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus.

In some embodiments, regulatable promoters may prove useful. Such promoters include for example, those that are hormone or cytokine regulatable. Hormone regulatable promoters include MMTV, MT-1, ecdysone and RuBisco as well as other hormone regulated promoters such as those responsive to thyroid, pituitary and adrenal hormones.

Another regulatory element contemplated for use in the present invention is an enhancer. These are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization. Enhancers useful in the present invention are well known to those of skill in the art and will depend on the particular expression system being employed (Scharf D et al (1994) *Results Probl Cell Differ* 20: 125–62; Bittner et al (1987) *Methods in Enzymol* 153: 516–544).

In certain embodiments of the invention, the expression construct comprises a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, In: Rodriguez R L, Denhardt D T, ed. Vectors: A survey of molecular cloning vectors and their uses. Stoneham: Butterworth, 467–492, 1988; Nicolas and Rubenstein, In: Vectors: A survey of molecular cloning vectors and their uses, Rodriguez & Denhardt (eds.), Stoneham: Butterworth, 493–513, 1988; Baichwal and Sugden, In: Gene Transfer, Kucherlapati R, ed., New York, Plenum Press, 117–148, 1986; Temin, In: gene Transfer, Kucherlapati (ed.), New York: Plenum Press, 149–188, 1986). The first viruses used as gene vectors were DNA viruses including the papovaviruses (simian virus 40, bovine papilloma virus, and polyoma) (Ridgeway, 1988 supra; Baichwal and Sugden, 1986 supra) and adenoviruses (Ridgeway, 1988 supra; Baichwal and Sugden, 1986 supra). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988, supra; Temin, 1986, supra).

D. Polyadenylation Signals.

Where an expression construct employs a cDNA insert, one will typically desire to include a polyadenylation signal sequence to effect proper polyadenylation of the gene transcript. Any polyadenylation signal sequence recognized by cells of the selected transgenic animal species is suitable for the practice of the invention, such as human or bovine growth hormone and SV40 polyadenylation signals.

Also contemplated as an element of the expression cassette is a terminator. These elements can serve to enhance message levels and to minimize read through from the cassette into other sequences. The termination region which is employed primarily will be one selected for convenience, since termination regions for the applications such as those contemplated by the present invention appear to be relatively interchangeable. The termination region may be native with the transcriptional initiation, may be native to the DNA sequence of interest, or may be derived for another source.

E. IRES.

In certain embodiments of the invention, the use of internal ribosome entry site (IRES) elements is contemplated to create multigene, or polycistronic, messages. IRES elements are able to bypass the ribosome scanning model of 5' methylated Cap dependent translation and begin translation at internal sites (Pelletier and Sonenberg, *Nature,* 334:320–325, 1988). IRES elements from two members of the picomavirus family (poliovirus and encephalomyocarditis) have been described (Pelletier and Sonenberg, 1988 supra), as well an IRES from a mammalian message (Macejak and Sarnow, *Nature,* 353:90–94, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

IV. Methods of Making Transgenic Animals

As noted above, a particular embodiment of the present invention provides transgenic animals heterozygous for a WFS1 mutation. Preferred animals exhibit characteristics associated with the pathophysiology of depression. Transgenic animals expressing mutant WFS1 transgenes, recombinant cell lines derived from such animals, and transgenic embryos may be useful in methods for screening for and identifying agents that will be useful in treating or otherwise intervening in the events that lead to clinical depression.

A. Animals Used.

In certain instances, it may be useful to set up a colony of mice for the production of transgenic mice and also for the production of colonies that may be employed for testing the effects of various antidepressant agents. The animals used as a source of fertilized egg cells or embryonic stem cells can by any animal. However, it is generally preferred that the host animal is one which lends itself to multi-generational studies. Transgenic animals may be produced from the fertilized eggs from a number of animals including, but not limited to reptiles, amphibians, birds, mammals, and fish. Within a particularly preferred embodiment, transgenic mice are generated which express a mutant form of the wolframin polypeptide which lacks the one or all of the potential transmembrane domains of wild-type wolframin. While this section generally discusses mouse colonies, it should be understood that similar considerations will apply to any animals that are employed in or generated according to the present invention.

The animals of a colony for the production and analysis of transgenic animals can be divided into five categories: female animals for matings to produce fertilized eggs; fertile stud males; sterile stud males for producing pseudo-pregnant females; female mice to act as pseudo-pregnant recipients and foster mothers; and transgenic animals, including founder animals and transgenic lines derived from such founders.

The C57BL/6J inbred strain of females are, to date, the most widely used for mating to produce the fertilized eggs. However, injection often can be performed with F2 hybrids generated from matings of F1 hybrid male and female mice (e.g., C57BL/6J,×CBA/J)F1 female×C57BL/6J,×CBA/J)F1 male). F2 hybrid zygotes from F1 hybrids have been successfully employed to produce transgenic mice. These F1 hybrids include but are not limited to C57BL/6J×CBA/J; C57BL/6J×SJL; C3H/HeJ×C57BL/6J; C3H/HeJ×DBA/2J and C57BL/6J×DBA/2J. Those of skill in the art will be aware of other strains of female mice from which fertile embryos could be generated. In certain embodiments, the transgenic mice of the present invention are created using ES cells from a 129sv mouse strain that are grown in 129sv females. These transgenic mice are then back crossed against C57BL/6 strain. In other embodiments, the knockouts are created in ES cells from C57BL/6 mice and implanted into pseudo-pregnant mice for gestation. In general, the generation of transgenic animals and their subsequent breeding is more efficient if F2 zygoytes are used for microinjection.

A colony for generating transgenic mice also contains fertile studs males. Such males are housed in a separate cages to avoid fighting and injury. These males should be placed in separate cages a few weeks prior to being presented to a superovulated female mouse that will be used for the production fertile eggs. This is necessary because the dominant male will suppress the testosterone and thus sperm production of his littermates. Each superovulated female is placed individually with a stud male.

Sterile males are required for mating to generate pseudo-pregnant recipients and usually are produced by vasectomy. Alternatively genetically sterile studs can be used. Pseudo-pregnant female mice are generated by mating females in natural estrus with vasectomized or genetically sterile males. Pseudo-pregnant females are is competent to receive embryos but do not contain any fertilized eggs. Pseudo-pregnant females are important for making transgenic animals since they serve as the surrogate mothers for embryos that have been injected with DNA or embryonic stem cells. The best pseudo-pregnant recipients are females that have already reared a litter of animals.

Mice that develop from the injected eggs are termed "founder mice". As soon as a founder mouse is identified it is mated to initiate the transgenic line. The potential founder transgenic mice are usually screened for the presence or absence of the injected gene by performing a Southern or dot blot hybridization to DNA extracted from the tail. The protein and RNA expression are analyzed and the transgene copy number and/or level of expression are determined using methods known to those of skill in the art. The protein, RNA expression, and transgene copy numbers are determined in weanling animals (4–5 weeks). When a promoter is used which is constitutively active in animals of weanling age and older, it is not expected that there will be changes in levels of transgenic RNA expression animals beyond weanling age. When a developmentally and/or tissue specific promoter is used, the protein levels are monitored to determine expression levels with age. The transgenic animals also are observed for clinical changes. Examples of neurobehavioral disorders for evaluation are poor mating response, agitation, diminished exploratory behavior in a novel setting, and inactivity may well be important behavioral traits associated with depression.

B. Methods of Making Transgenic Animals.

A transgenic animal can be prepared in a number of ways. A transgenic organism is one that has an extra or exogenous fragment of DNA incorporated into its genome, sometimes replacing an endogenous piece of DNA. At least for the purposes of this invention, any animal whose genome has been modified to introduce a WFS1 nutation, as well as its mutant progeny, are considered transgenic animals. In order to achieve stable inheritance of the extra or exogenous DNA, the integration event must occur in a cell type that can give rise to functional germ cells. The two animal cell types that are used for generating transgenic animals are fertilized egg cells and embryonic stem cells. Embryonic stem (ES) cells can be returned from in vitro culture to a "host" embryo where they become incorporated into the developing animal and can give rise to transgenic cells in all tissues, including germ cells. The ES cells are transfected in culture and then the mutation is transmitted into the germline by injecting the cells into an embryo. The animals carrying mutated germ cells are then bred to produce transgenic offspring. The use of ES cells to make genetic changed in the mouse germline is well recognized. For a reviews of this technology, those of skill in the art are referred to Bronson and Smithies, *J. Biol. Chem.*, 269(44), 27155–27158, (1994); Torres, *Curr. Top. Dev. Biol.*, 36, 99–114; 1998 and the references contained therein.

Generally, blastocysts are isolated from pregnant mice at a given stage in development, for example, the blastocyst from mice may be isolated at day 4 of development (where day 1 is defined as the day of plug), into an appropriate buffer that will sustain the ES cells in an undifferentiated, pluripotent state. ES cell lines may be isolated by a number of methods well known to those of skill in the art. For example, the blastocysts may be allowed to attach to the culture dish and approximately 7 days later, the outgrowing inner cell mass picked, trypsinized and transferred to another culture dish in the same culture media. ES cell colonies appear 2–3 weeks later with between 5–7 individual colonies arising from each explanted inner cell mass. The ES cell lines can then be expanded for further analysis. Alternatively, ES cell lines can be isolated using the immunosurgery technique (described in Martin, *Proc. Natl. Acad. Sci. USA* 78:7634–7638 (1981)) where the trophectoderm cells are destroyed using anti-mouse antibodies prior to explanting the inner cell mass.

In generating transgenic animals, the ES cell lines that have been manipulated by homologous recombination are reintroduced into the embryonic environment by blastocyst injection (as described in Williams et al., *Cell* 52:121–131 (1988)). Briefly, blastocysts are isolated from a pregnant mouse and expanded. The expanded blastocysts are maintained in oil-drop cultures at 4° C. for 10 min prior to culture. The ES cells are prepared by picking individual colonies, which are then incubated in phosphate-buffered saline, 0.5 mM EGTA for 5 min; a single cell suspension is prepared by incubation in a trypsin-EDTA solution containing 1% (v/v) chick serum for a further 5 min at 4° C. Five to twenty ES cells (in Dulbecco's modified Eagle's Medium with 10% (v/v) fetal calf serum and 3,000 units/ml DNAase 1 buffered in 20 mM HEPES [pH 8]) are injected into each blastocyst. The blastocysts are then transferred into pseudo-pregnant recipients and allowed to develop normally. The transgenic mice are identified by coat markers (Hogan et al., Manipulating the Mouse Embryo, Cold Spring Harbor, N.Y. (1986) ). Additional methods of isolating and propagating ES cells may be found in, for example, U.S. Pat. No. 5,166,065; U.S. Pat. No. 5,449,620; U.S. Pat. No. 5,453,357; U.S. Pat. No. 5,670,372; U.S. Pat. No. 5,753,506; U.S. Pat. No. 5,985,659, each incorporated herein by reference.

An alternative method involving zygote injection method for making transgenic animals is described in, for example, U.S. Pat. No. 4,736,866, incorporated herein by reference. Additional methods for producing transgenic animals are generally described by Wagner and Hoppe (U.S. Pat. No. 4,873,191; which is incorporated herein by reference), Brinster et al. *Proc. Nat'l Acad. Sci. USA*, 82(13) 4438–4442, 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

Briefly, this method involves injecting DNA into a fertilized egg, or zygote, and then allowing the egg to develop in a pseudo-pregnant mother. The zygote can be obtained using male and female animals of the same strain or from male and female animals of different strains. The transgenic animal that is born, the founder, is bred to produce more animals with the same DNA insertion. In this method of making transgenic animals, the new DNA typically randomly integrates into the genome by a non-homologous recombination event. One to many thousands of copies of the DNA may integrate at a site in the genome Generally, the DNA is injected into one of the pronuclei, usually the larger male pronucleus. The zygotes are then either transferred the same day, or cultured overnight to form 2-cell embryos and then transferred into the oviducts of pseudo-pregnant females. The animals born are screened for the presence of the desired integrated DNA.

DNA clones for microinjection can be prepared by any means known in the art. For example, DNA clones for microinjection can be cleaved with enzymes appropriate for removing the bacterial plasmid sequences, and the DNA fragments electrophoresed on 1% agarose gels in TBE buffer, using standard techniques. The DNA bands are visualized by staining with ethidium bromide, and the band containing the expression sequences is excised. The excised band is then placed in dialysis bags containing 0.3 M sodium acetate, pH 7.0. DNA is electroeluted into the dialysis bags, extracted with a 1:1 phenol:chloroform solution and precipitated by two volumes of ethanol. The DNA is redissolved in 1 ml of low salt buffer (0.2 M NaCl, 20 mM Tris, pH 7.4, and 1 mM EDTA) and purified on an Elutip-D™ column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind DNA to the column matrix. After one wash with 3 ml of low salt buffer, the DNA is eluted with 0.4 ml high salt buffer and precipitated by two volumes of ethanol. DNA concentrations are measured by absorption at 260 nm in a UV spectrophotometer. For microinjection, DNA concentrations are adjusted to 3 mg/ml in 5 mM Tris, pH 7.4 and 0.1 mM EDTA.

Additional methods for purification of DNA for microinjection are described in Hogan et al. Manipulating the Mouse Embryo (Cold Spring Harbor Laboratory, Cold Spring Harbor, N.Y., 1986), in Palmiter et al. *Nature* 300:611 (1982); in The Qiagenologist, Application Protocols, 3rd edition, published by Qiagen, Inc., Chatsworth, Calif.; and in Sambrook et al. Molecular Cloning: A Laboratory Manual (Cold Spring Harbor Laboratory, Cold Spring Harbor, N.Y., 1989).

In an exemplary microinjection procedure, female mice six weeks of age are induced to superovulate. The superovulating females are placed with males and allowed to mate. After approximately 21 hours, the mated females are sacrificed and embryos are recovered from excised oviducts and placed in an appropriate buffer, e.g., Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA in a 37.5° C. incubator with a humidified atmosphere at 5% $CO_2$, 95% air until the time of injection. Embryos can be implanted at the two-cell stage.

Randomly cycling adult female mice are paired with vasectomized males. C57BL/6 or Swiss mice or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipette (about 10 to 12 embryos). The pipette tip is inserted into the infundibulum and the embryos transferred. After the transfer, the incision is closed by two sutures. The pregnant animals then give birth to the founder animals which are used to establish the transgenic line.

V. Methods of Using Transgenic Cell and Animals

Transgenic animals and cell lines derived from such animals will find use in drug screening experiments. In this regard, heterozygotic WFS1 mutant transgenic animals and cell lines capable of expressing the mutant WFS1 gene will be exposed to test substances, to screen the test substances for the ability to decrease symptoms of depression, alter serotonin re-uptake or improve some other parameter normally associated with clinical depression. Therapeutic compounds identified by such procedures will be useful in the treatment of depression. Alternatively, the animals and cell lines may be useful for monitoring the effects of known antidepressants.

It is contemplated that this screening technique will prove useful in the general identification of a compound that will serve the purpose of overcoming, circumventing or otherwise abolishing the effects of wolframin deficit seen in wolframin heterozygotes. Such compounds may be useful in the treatment of various disorders related to wolframin syndrome as well as for the treatment of depression and depressive disorders.

A. In Vitro Formats

In certain embodiments, the present invention is directed to a method for determining the ability of a candidate substance to overcome wolframin deficiency. The method includes generally the steps of:

(i) providing a transgenic cell comprising a WFS1 knockout genotype;

(ii) contacting said transgenic cell with a candidate substance; and (iii) comparing the WFS1 activity of the transgenic cell of step (ii) with the activity observed in the absence of the candidate substance, wherein an alteration in WFS1 activity indicates that said candidate substance is a modulator of said activity.

To identify a candidate substance as being capable of modulating WFS1 activity in the assay above, one would measure or determine the activity in the absence of the added candidate substance. One would then add the candidate substance to the cell and determine the activity in the presence of the candidate substance. A candidate substance which increases the activity relative to that observed in its absence is indicative of a candidate substance with stimulatory capability. Such studies also may be conducted in parallel, where one assay monitors the activity in the presence of the candidate substance and a similar assay monitors the activity in the absence of the substance.

The candidate screening assays are simple to set up and perform. Thus, in assaying for a candidate substance, after obtaining the transgenic cell, one will admix a candidate substance with the cell, under conditions which would allow measurable parameter of wolframin deficiency to occur. In this fashion, one can measure that parameter in the absence of the candidate substance and compare the ability of the candidate substance to overcome the lack of wolframin in the cell by monitoring the same parameter in the presence of the candidate substance.

Significant changes in depression related events include an increased e.g., serotonin re-uptake, changes in depression related events including decreased levels of brain derived neurotrophic factor mRNA in the brain (especially the hippocampus); increased levels of corticotrophin-releasing factor in cerebrospinal fluid; increased levels of arginine vasopressin mRNA in the paraventricular nucleus, or increased levels of corticosterone in serum and the like and are represented by an increase/decrease in activity of at least about 30%–40%, and most preferably, by changes of at least about 50%, with higher values of course being possible.

The transgenic cell lines of the present invention are amenable to numerous high throughput screening (HTGS) assays known in the art. Automated and miniaturized HTGS assays are also contemplated as described for example in Houston and Banks *Curr. Opin. Biotechnol.* 8: 734–740 (1997).

B. In Vivo Formats.

Preferred transgenic animals of the invention will, as a population, exhibit a statistically significant increased probability of exhibiting signs of depression, when compared with non-transgenic littermates. An increased probability of exhibiting signs of depression means that, in a population of the transgenic animals, a greater percentage of the animals will exhibit measurable symptoms of depression compared to non-transgenic animals, such as non-transgenic littermates. Various methods of determining symptoms of depression are described herein below, and methods of determining statistical- significance are well known in the art.

The transgenic mouse of the present invention has a variety of different uses. First, by creating an animal model in which the function of WFS1 has been altered, the present inventors have provided a living system in which the function of WFS1 may be further determined. For example, provision of various forms of WFS1—deletion mutants, substitution mutants, insertion mutants, fragments and wild-type proteins—labeled or unlabeled, will permit numerous studies on depression that were not previously possible.

The transgenic mice of the present invention will thus be used to identify modulators of depression. The presence of a heterozygous WFS1 phenotype in the transgenic mouse represents a mouse model for depression. Treatment of a transgenic mouse with a putative antidepressants, and comparison of the depressed response of this treated mouse with the untreated transgenic animals or transgenic animals treated with a known antidepressant, or normal controls, provides a means to evaluate the activity of the candidate antidepressant. Another use for the transgenic mouse of the present invention is in the in vivo identification of a modulator of WFS1 activity.

Treatment of animals with test compounds will involve the administration of the compound, in an appropriate form, to the animal. Administration will be by any route the could be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intracerebroventricular, intraperitoneal or intravenous injection. Specifically contemplated are systemic intravenous injection, regional administration via blood or lymph supply and systemic administration through the diet.

Determining the effectiveness of a compound in vivo may involve a variety of different criteria. Such criteria include, but are not limited to, survival, improved performance in forced swim tests, improved performance in tail suspension test, improved food intake or any other determinant of depression.

C. Compounds Tested.

The present invention provides screening assays to identify agents which overcome wolframin deficiency and/or have a beneficial antidepressant effect, As used herein the term "candidate substance" refers to any molecule or composition that one wishes to screen for the ability to modulate behavioral or biochemical characteristics of depression; or the ability to modulate activity in a wolframin deficient system. In specific embodiments, the molecule is screened to determine if it helps to alleviate or overcomes wolframin deficiency in wolframin heterozygotes. In preferred embodiments, the candidate substance is screened for antidepressant properties.

The candidate substance may be a protein or fragment thereof, a small molecule susceptible to laboratory synthesis, or even a nucleic acid molecule. Screening of compounds that are structurally related to other known antidepressants is particularly contemplated. The active compounds may include fragments or parts of naturally-occurring compounds or may be only found as active combinations of known compounds which are otherwise inactive.

Compounds isolated from natural sources, such as animals, bacteria, fungi, plant sources, including leaves and bark, and marine samples may be assayed as candidates for the presence of such potentially useful pharmaceutical agents. Alternatively, the agents to be screened could also be man-made compounds. Thus, the candidate substance identified by the present invention may be polypeptide, polynucleotide, small molecule inhibitors or any other compounds that may be designed through rational drug design starting from known effectors of depression.

Of particular interest as starting points to designing new antidepressants that can be tested using the animals or cells of the present invention are those compounds already known to have potential antidepressant activity. Such compounds include but are not limited to serotonin re-uptake inhibitors (SSRI), such as sertraline (registered trademark ZOLOFT, Pfizer), fluoxetine (PROZAC—Eli Lilly), paroxetine (PAXIL—Smith Kline Beecham) and fluvoxamine (LWOX); tricyclic antidepressants such as ELAVIL (Merck, Sharpe and Dohme), and aminoketone antidepressants such as bupropion.

Additionally, there are a number of different libraries that may prove useful in the identification of small molecule antidepressants including chemical libraries, natural product libraries and combinatorial libraries comprised or random or designed peptides, oligonucleotides or organic molecules.

Chemical libraries consist of structural analogs of known compounds or compounds that are identified as hits or leads via natural product screening or from screening against a potential therapeutic target.

Natural product libraries are collections of products from microorganisms, animals, plants, insects or marine organisms which are used to create mixtures of screening by, e.g., fermentation and extractions of broths from soil, plant or marine organisms. Natural product libraries include polypeptides, non-ribosomal peptides and non-naturally occurring variants thereof. For a review see *Science* 282:63–68 (1998).

Combinatorial libraries are composed of large numbers of peptides oligonucleotides or organic compounds as a mixture. They are relatively simple to prepare by traditional automated synthesis methods, PCR cloning or other synthetic methods. A review of combinatorial libraries and libraries created therefrom, see Myers *Curr. Opin. Biotechnol.* 8: 701–707 (1997). A candidate antidepressant agent identified by the use of various libraries described may then be optimized to modulate its antidepressant activity through, for example, rational drug design.

D. Assays for Depression.

Preferred transgenic animals of the present invention will be useful as models of depression because such animals perform differently when compared wild-type animals or those animals that have been given antidepressant medication. Generally, "performs differently" means that the transgenic animals will be less active, more despairing, less willing to escape dangerous conditions or have neurochemical measurements that are indicative of the depressed animal. These animals will be useful in assisting in monitoring the pathological progress of depression as well as in the identification of new antidepressant compounds.

There are a variety of behavioral assays that can be employed in monitoring depression in animals. These assays include, for example, the forced swimming wheel test (Porsolt, *Eur. J. Pharmacology,* 47, 379–391, 1978; Kasahara, et al., *Life Sci.,* 52(22):1741–1749 1993) and the tail suspension test described by Teste, et al., *Fundam. Clin. Pharmacol.,* 7(5):219–226 (1993).

The forced swim test is a standard test used to screen compounds for anti-depressant like activity and was originally described using rats. (Porsolt *Eur. J. Pharmacology,* 47, 379–391, 1978). Subsequently, the assay has been modified for use in mice (Kasahara, et al., *Life Sci.,* 52(22):1741–1749 1993). Briefly, in the Porsolt test, swim sessions are conducted by placing animals in plastic containers containing 16 inches of water at 23° C. to about 25° C. This level of water is selected to be deep enough so that the animal cannot touch the bottom with its hindlimbs or tail, nor can it escape. Two swim sessions are conducted, an initial 15 minute pretest one day prior to administration of the antidepressant drug and a second 5 minute test after infusion of the drug into the midbrain is begun. Each animal's 5 minute test sessions are videotaped for scoring later. The amount of time the animal spends active (swimming, exploring or trying to escape) and the time the rat is immobile (not struggling and making only those movements necessary to keep its head above water) is measured. Drugs with anti-depressant like activity decrease the immobility time.

The Kasahara test is a modification of the above Porsolt test in that it employs a water wheel instead of a cylinder (Kasahara, et al., *Life Sci.,* 52(22):1741–1749 1993; Nomura et al., *Eur. J. Pharmacol.* 83(3–4) 171–175, 1982). Essentially a water wheel is placed in a water tank. Mice are placed on the apparatus so that they run on the wheel making it turn. If the mice try and "escape" from the water, they turn the wheel vigorously, when the mice begin to despair, they stop running and the wheel stops turning. Thus the number of turns of the wheel are indicative of level of depression of the animal. A few hours before the test, the control and treatment groups of mice, respectively, receive subcutaneous injections of placebo or drug to be tested. The mice are individually placed in the swimming wheel and the number of turns of the wheel is recorded for each. Antidepressant activity is indicated by an increased number of turns in the treatment group An additional procedure for monitoring the effects of antidepressants involves suspending the mice by the tail from a lever and recording movements of the animal. The total duration of the test (usually about 6 minutes) can be divided into periods of agitation and immobility. Antidepressants will generally decrease the duration of immobility (Steru et al., *Psychopharmacology* 85(3) 367–70). A computerized version of this test, referred to as ITEMATIC-TST has been developed and is well known to those of skill in that art as a primary screening test for antidepressant activity (Steru et al., *Prog. Neuropsychpharmacol. Biol. Psychiatry* 11(6)659–671, 1987). Additional devices for monitoring depression also are known to those of skill in the art (Nomura et al., *Yakubutsu Seishiiz Kodo* 12(5)207–13, 1992).

As mentioned above, in monitoring depression in test animals, it may be necessary to supplement the tail suspension test or the forced swimming tests with measurements to ensure that the immobility is not due to loss of locomotor function. Assays for monitoring locomotor function also are well known to those of skill in the art. In an exemplary assay, locomotor testing involves monitoring rotational behavior of the transgenic animals with an automated rotational monitor (Rota-Count 8, Columbus Instruments, Columbus, Ohio) with or without the administration of the antidepressant. The animals are fitted with a cloth harness and placed in an individual cylindrical transparent plexiglass cage (12 inch diameter×16 inch height). The harness is attached to a rotational sensor on the cage lid via a stainless steel cabled tether. Partial (60 degree) rotations are recorded for both clockwise (ipsiversive to the infused hemisphere) and counter-clockwise (contraversive to the infused hemisphere) directions for 80 minutes.

In order to demonstrate that general changes in locomotor activity could not account for the reduction of immobility time in the forced swim test or the tail suspension test, changes in locomotor activity are monitored. If no changes in locomotor activity are produced as measured by 60° partial rotation behavior then the immobility of the animals in the swim or suspension tests is not due to loss of locomotor function. Of course, as additional activities of wolframin are identified it may be that the knockout function also may have some effect on the locomotor brain function and thus the results from locomotor function assay may prove useful even in the absence of conducting the swim and/or suspension tests.

The elevated plus maze test is another behavioral test that is commonly employed by those of skill in the art and may be employed in the present invention to monitor the behavior of the transgenic mice both in comparison to non-transgenic animals as well as to transgenic animals treated with antidepressant agents. In this test a four arm radial maze consisting of two opposing enclosed arms (e.g., 30 cm high×30 cm long×5 cm wide) and two opposing exposed arms (30 cm×5 cm) is elevated on a pedestal 30 cm above the surface of a table and situated in the center of a dimly lit room. Computer interfaced, infrared photocell beams situated around the perimeter and diagonally across the center of the maze are employed to monitor the amount of time spent in each compartment and provided a gross measure of overall activity. The mice are placed in the center of the maze facing an enclosed arm to begin the five minute test period. The effects of the drugs are monitored a suitable time after administration of the candidate substance. Relative performance in this test will reveal whether the candidate substance has a positive effect in alleviating depression.

Additionally, the response of the mice to novel environment also may be monitored. In a typical assay, a plexiglass box (e.g., 33 cm long×23 cm wide×20 cm high) is equipped with computer interfaced, infrared photocell beams which trisect the length of the chamber. Mice which have not previously experienced this testing environment are allowed to explore the box for 30 minutes during which time horizontal locomotor activity as well as movement from one end of the box to the other is recorded. Experiments designed to test the effect of social defeat stress are performed 3–5 minutes following exposure of the test animal to the stressor. The social defeat stress consists of a brief encounter between a test male (intruder) and a resident male (resident) which has been housed with a family comprised of a female and pups. The resident-intruder interaction takes place in the resident male cage and in all cases, the intruder is placed in the cage for <1 minute. At the first sign of aggressive behavior between the two animals, the intruder male is removed from the resident cage and housed singly for 3–5 minutes before placement into the novel environment chamber to measure locomotor activity. These locomotor activity will be useful in assisting a determination of the general behavioral characteristics of the animals in the presence and absence of the test compounds as well as determining the differences between transgenic and non-transgenic animals. Additional behavioral tests that may also be advantageously employed in the present invention will be known to those of skill in the art.

In addition to the behavioral assays described above, those of skill in the art could monitor chronic stress-induced neurochemical changes. In such an assay, on would perform neurochemical measurements in which serotonin levels were monitored as a function of stress induction. Serotonin and its principle metabolite, 5-hydroxyindole-acetic acid (5-HIAA), can be measured using an isocratic HPLC elution system and electrochemical detection, using a 16 channel coulometric array detector according to methods well known to those of skill in the art (ESA, Inc., Bedford, Mass.; Gamache et al, *Neurosci. Abstracts* 17:985,1991).

Significant changes in depression-related events used to characterize depression-like behavior of the heterozygous animals include decreased levels of brain-derived neurotrophic factor mRNA or protein in the brain, especially in the hippocampus; increased levels of corticotrophin-releasing factor in then cerebrospinal fluid; increased levels or arginine vasopressin mRNA or protein in the paraventicular nucleus; increased hypothalamic pituitary axis activity; resistance to suppression of ACTH by dexamethasone; cognitive disturbances; or increased levels of corticosterone in serum. Anti-depressant therapy would be expected to reverse, at least partially, these changes.

VI. EXAMPLES

The following example presents preferred embodiments and techniques, but is not intended to be limiting. Those of skill in the art will, in light of the present disclosure, appreciate that many changes can be made in the specific materials and methods which are disclosed and still obtain a like or similar result without departing from the spirit and scope of the invention.

Example 1

Construction of a WSF1 Knockout Vector

Figure 2:
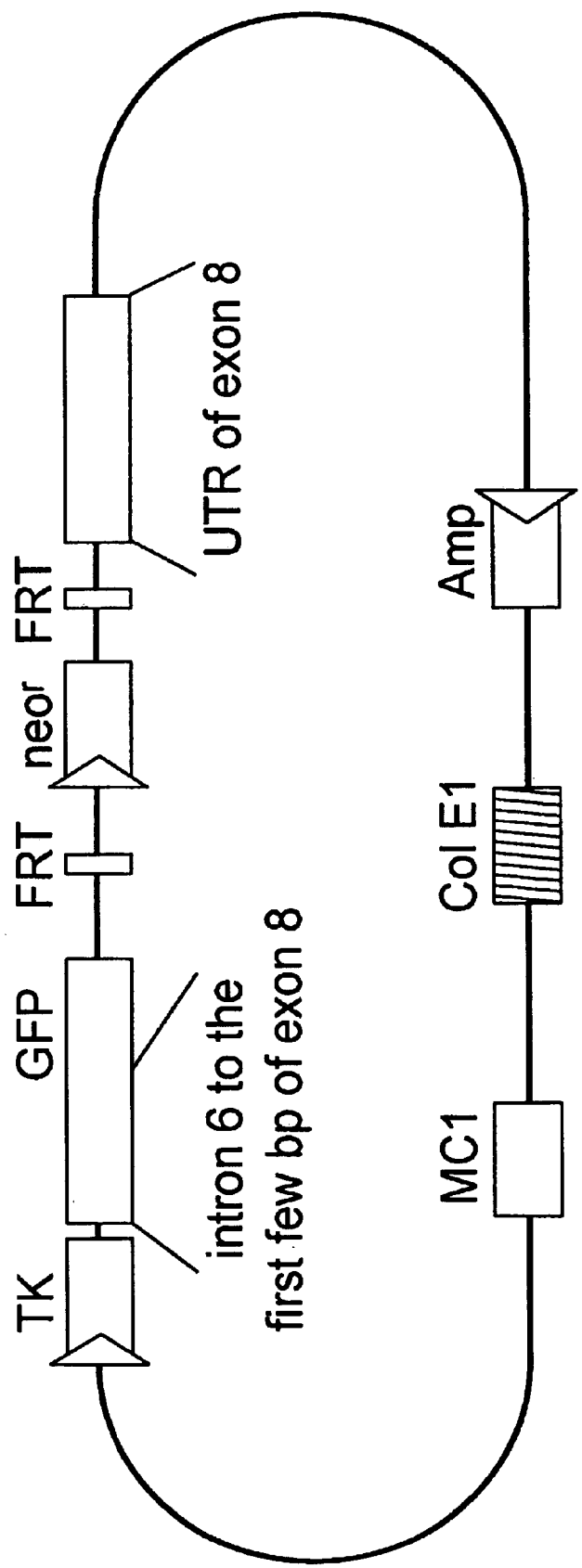
FIG. 2. shows an exemplary WFS1 knockout construct for homologous recombination.

This example details exemplary methods and compositions for constructing WFS1 vectors to be used in making the animals accordance with the present invention. An exemplary WFS1 knockout vector for use in homologous recombination is depicted in FIG. 2 which comprises the tk negative selection marker, a region comprising a region from intron 6 through to the first few base pairs of exon 8 linked to a GFP marker, a neomycin resistance marker and the UTR of exon 8.

The following procedure was conducted to isolate a mouse genomic clone containing at least a substantial portion of the murine WFS1 gene, for use in designing a vector to create transgenic WFS1 mutants. Oligonucleotide PCR primers were designed based on the mouse cDNA sequences and a human WFS1 genomic map that would be predicted to be within exons 2 and 8. These exons were chosen because they were large enough to yield large PCR products and because they contained the 5'→3' ends of the translated sequence, respectively. The primers were used to amplify DNA fragments from mouse genomic DNA. Primers within exon 8 were used to screen the SJ129/OLA genomic DNA library in a P1 vector (Genome Systems, St. Louis, Mo.). This screening identified a clone that contained exon 2 and 8 of the mouse WFS1 gene. This P1 clone contained the mouse WFS1 gene. The 10 kb region of DNA surrounding exon 8 was sequenced. This clone and sequence data were then used to construct a WFS1 knockout mouse using the methods described herein (FIG. 1).

P1 DNA was used as template for walking primer DNA sequencing to extend sequence information in the 5' and 3' directions from exon 8. The initial primers were designed from the mouse WFS1 cDNA (GenBank accession #AJ011971) at regions predicted to be located near the intron 7/exon 8 junction and near the end of the 3' untranslated region. Successive primer walking steps were used to generate a total of 4.78 and 3.54 kb of new mouse genomic sequence data. About 6 kb of this new sequence information was obtained from both DNA strands thereby ensuring greater accuracy of the sequence data.

BLAST searching of the 5' end of exon 8 showed that the sequence isolated from the primer walking steps included exons 6 and 7 of the mouse gene. Hence indicating that the mouse gene is smaller that the human WFS1 gene. The mouse introns are 1.47 and 2.88 kb respectively. Exon 8 contains the majority of the WFS1 polypeptide coding region encoding 601 of the 890 amino acid residues and a 0.8 kb 3' untranslated region. The primers and methods employed to perform these investigations are described in further detail below.

Vector: The pKO Scrambler NTK Vector #901 was purchased from Stratagene, La Jolla, Calif. This vector has two separate multiple cloning sites that allow for the directional subcloning of the 5' and 3' arms of homology. The vector is derived from pUC19 and carries the genes for neomycin phosphotransferase and thymidine kinase, allowing for both positive and negative selection.

Primers and PCR Conditions: Primers were designed based on the predicted exon 8 portion of the WFS1 DNA and used to screen a mouse ES cell 129/OLA genomic DNA library in a P1 vector. This screening yielded a clone (control number 21041) that was received in E. coli strain NS3529. The P1 clone was transferred to strain NS3516 and 27.5 µg of P1 DNA was isolated.

In order to confirm the presence of the WFS1 genomic DNA, primers were designed based on predicted exons 2 and 8 of the mouse WFS1 cDNA (GenBank AF084482 and AJ011971); the following primers were designed: for exon 2: 5'-GCCCGGGCCCGGCTCAAT-3' (MWSF1F; SEQ ID NO:2) and 5'-TTCTTCCCGGCTGCCGGTTTGA-3' (MWSF1R; SEQ ID NO:3); for exon 8: 5'-ATCTGCGGCGTACCCCTGCTTTTC-3' (MWSF2F; SEQ ID NO:4) and 5'-GTCCGGGCCATGTTAGTTTCCTTC-3' (MWSF2R; SEQ ID NO:5)

PCR was performed using mouse genomic DNA, P1 vector, or clone 21041 as templates. Thermal cycling consisted of 10 min at 95° C., 30 cycles of (30 sec at 94° C., 30 sec at 60° C., and 1 min at 72° C.), 10 min at 72° C., and optionally 4° C. overnight. This PCR analysis confirmed that the 21041 P1 clone contained at least exons 2 and 8 of the WFS1 DNA. The P1 clone was sequenced and found to contain the sequence extending from exon 6 into the 3' untranslated region of the murine WFS-1 gene.

Two primer sets were designed to produce the 5' arm of the targeting construct, which was referred to as Fragment A. This included sequence from intron 6 up to the first 18 bases of exon 8 in WFS-1 fused to Green Fluorescent Protein cDNA and a FRT recognition site for Flp recombinase.

The first primer, MWF-1, was designed from sequence in intron 6 and introduced a Hind III restriction site and included a naturally occurring Hpa I restriction site. The sequence is:
5' GTCAAGCTTCTGACTCATCATGT-TAACTCCCGAGTGCAGCC (SEQ ID NO:6).
The second primer of this pair, MWF-2, was designed to fuse exon 8 to Green Fluorescent Protein starting after the initiating methionine. The sequence of MWF-2 is 5' AGCTCCTCGCCCTTGCTCACTAAAGGG-TACTTCACCAC (SEQ ID NO:7). The product of PCR using MWF-1 and MWF-2 represented the 5' portion of Fragment A.

The primer pair MWF-3 and MWF-4 produced the 3' end of Fragment A. MWF-3 was the reverse of MWF-2 and MWF-4 was specific for a region that included the polyadenylation signal sequence for Green Fluorescent Protein and a FRT recognition site specific for Flp recombinase. The sequences are as follows: 5' GTGGTGAAGTACCCTT-TAGTGAGCAAGGGCGAGGAGCT (MWF-3; SEQ ID NO:8) and 5' GAGTGAATTCCTCGAGGGAAGTTC-CTATTCGGAAGTTCCTATTCTTCTAGA AGTATAG-GAACTTCAGTTTGGACAAACCACAACTA-GAATGCAGTG (MWF-4; SEQ ID NO:9).

The 3' arm of the targeting construct (Fragment B) was generated by the primer pair MWF-5 and MWF-6. MWF-5 included a second FRT recognition site fused to genomic sequence that was 3' of the WFS-1 gene. MWF-6 corresponded to genomic sequence that was about 3100 base pairs downstream of MWF-5. The sequences of these primers are:
5'GCTGGTACCATCGATGAAGTTC-CTATACTTCTAGAAGAATAGGAACTTC CGAATAG-GAACTTCCAACATAGTATGTATGAACCCAGATTC (MWF-5; SEQ ID NO:10) and
5' GTTGCAAGCTTCCCGGGCTGACAACTTG-GCAATCACCTTGTGAG (MWF-6; SEQ ID NO:11).

For PCR, the Advantage-GC cDNA PCR kit from Clonetech was used. This kit is specially designed for the amplification of GC-rich templates. PCR reactions included 40 mM tricine-KOH (pH 9.2), 15 mM KOAc, 3.5 mM $Mg(OAc)_2$, 5% dimethyl sulfoxide, 3.75 µg/ml bovine serum albumin, 0.5 M "GC-Melt, 10 ng of template DNA, 0.25 µM primers, 0.2 mM dNTPs, and 1 µl of Advantage-GC cDNA Polymerase mix. A MJ Research PTC-100 thermocycler was used with an initial denaturation step of 95° C. for 2 min followed by 5 cycles of 94° C. for 30 sec, 55° C. for 45 sec, and 72° C. for 5 min. This was followed by 25 cycles of 94° C. for 30 sec, 65° C. for 45 sec, and 72° C. for 5 min. A final 5 min extension at 72° C. was followed by holding the reaction at 4° C. The P1 clone containing the murine WFS1 gene (control number 21041) was used as the DNA template for PCR using MWF-1 and MWF-2 or using MWF-5 and MWF-6 as primer pairs. The plasmid pEGFP-1 from Clonetech was used as the template for amplifying Green Fluorescent Protein cDNA sequences with primers MWF-3 and MWF-4.

Ligation and Subcloning: Aliquots of the PCR products were gel purified on a 0.8% agarose gel. The appropriate bands were excised, purified, and quantitated by UV absorption spectrophotometry. To generate Fragment A from the products of PCR using MWF-1 with MWF-2 and MWF-3 with MWF-4, an additional PCR was run as described above using the primers MWF-1 and MWF-4. The template consisted of 20 ng of product from the PCR reactions of MWF-1 with MWF-2 and MWF-3 with MWF-4. This reaction product was gel purified and ligated into the pKO Scrambler NTK vector.

After Fragment A was subcloned, Fragment B was also gel purified and ligated into the vector. One Shot TOP10 competent cells from Invitrogen were transformed with the final targeting construct. Plasmid was purified from these cells using a Qiagen DNA purification column. Double stranded sequencing analysis revealed a 500 bp region that contained 27 errors presumably introduced by PCR. These were contained in the Fragment A. An examination of Fragment A revealed two unique restriction sites that could be used to replace a 1600 bp portion of this insert that contained the region with the errors. The conditions of the PCR were changed in an attempt to enhance the fidelity of the polymerase. A new 1600 bp insert was generated and inserted in the construct to repair the errors. The above methods were used to generate a vector for use in homologous recombination as depicted in FIG. 1 and FIG. 2.

Design of Screening Primers: Primers were designed for use in a primary screen to look for homologous recombinants. The primer MWF-SC1 is based on vector sequence that is 47 base pairs upstream of the 5' end of Fragment B. The sequence of MWF-SC1 is 5'GCGCATGCTCCAGACT-GCCTTG (SEQ ID NO:12). The other primer for this screen is MWF-SC2. In order to screen for a sequence that would be in the genome and not in the targeting vector, the last 100 base pairs of the targeting construct were removed by using the two blunt end restriction sites Swa I and Sma I. Since these were both blunt end sites the vector was religated after the digest. MWF-SC2 is based on a portion of the 100 base pair fragment that was cut out so that the sequence for this primer is no longer in the targeting construct and will, therefore, be unaffected by a recombination event. The sequence of MWF-SC2 is 5' CTGACAACTTGGCAAT-CACCTTGTGAG 3' (SEQ ID NO: 13).

A summary of the identity of the sequences discussed above is as follows: SEQ ID NO:1: mouse WFS1 genomic DNA sequence; SEQ ID NO:2: forward primer specific for exon 2 of mouse WFS1; SEQ ID NO:3: reverse primer specific for exon 2 of mouse WFS1; SEQ ID NO:4: forward primer specific for exon 8 of mouse WFS1; SEQ ID NO:5: reverse primer specific for exon 8 of mouse WFS1; SEQ ID NO:6: primer sequence designed from a sequence in intron 6 to introduce a Hind III restriction site and included a naturally occurring Hpa I restriction site; SEQ ID NO: 7: primer MWF-2 designed to fuse exon 8 to Green Fluorescent Protein starting after the initiating methionine; SEQ ID NO:8: reverse primer for MWF-2; SEQ ID NO:9: primer MWF-4 specific for a region that includes the polyadenylation signal sequence for Green Fluorescent Protein and a FRT recognition site specific for Flp recombinase; SEQ ID NO:10: primer MWF-5 which includes a second FRT recognition site fused to genomic sequence from 3' of the WFS-1 gene; SEQ ID NO:11: primer MWF-6 corresponding to a genomic sequence about 3100 base pairs downstream of MWF-5; SEQ ID NO:12: primer designed to screen for homologous recombinants based on vector sequence 47 base pairs upstream of the 5' end of Fragment B; SEQ ID NO:13: MWF-SC2 primer designed to screen for a sequence that would be in the genome and not in the targeting vector.

While the methods and compositions herein have been described in terms of preferred embodiments, it will be apparent that variations may be applied to the methods and/or compositions without departing from the concept, spirit and scope of the invention. More specifically, it will be apparent that assays which are physiologically related may be substituted for the assays described herein while still producing the same or similar results. All such similar substitutes and modifications apparent to those of skill in the art are deemed to be within the scope of the invention as defined by the appended claims.

To the extent that certain exemplary procedural or other details supplementary to those described herein may be found in the references cited herein, such references are all specifically incorporated herein by reference.

What is claimed is:

1. A transgenic mouse selected from the group consisting of:
   a transgenic mouse comprising a genome containing a single copy of a wild-type wolframin (WFS1) gene and a WFS1 allele modified to contain a null mutation (null allele); and progeny thereof that are heterozygous for said null allele,
   wherein said transgenic mouse exhibits increased vulnerability to stress compared to a similar mouse comprising a homozygous wild-type WFS1 genotype, as measured in at least one behavioral assay selected from the group consisting of a forced swim assay, a tail suspension assay, a learned helplessness assay, and a responsivity to reward assay.

2. The transgenic mouse according to claim 1, wherein administration to said mouse of at least one antidepressant selected from the group consisting of a serotonin-selective re-uptake inhibitor; norepinephrine re-uptake inhibitor; tricyclic antidepressant; and monoamine oxidase inhibitor correlates with an improved performance in at least one assay selected from the group consisting of a forced swim assay, a tail suspension assay, a learned helplessness assay, and a responsivity to reward assay.

3. The transgenic mouse of claim 1, wherein said mouse exhibits chronic stress-induced reduction in BDNF levels associated with depression as compared to a similar mouse comprising a homozygous wild-type WFS1 genotype.

4. The transgenic mouse according to claim 3, wherein administration of at least one antidepressant selected from the group consisting of a serotonin-selective re-uptake inhibitor; norepinephrine re-uptake inhibitor; tricyclic antidepressant; and monoamine oxidase inhibitor to said mouse correlates with increased BDNF levels in said mouse as determined by an assay that monitors BDNF levels.

5. The transgenic mouse of claim 1, wherein said null mutation is selected from the group consisting of a deletion mutation, an insertion mutation, a non-sense mutation or a missense mutation.

6. The transgenic mouse of claim 5, wherein the null mutation is a deletion mutation.

7. The transgenic mouse of claim 1, wherein said null allele lacks a nucleotide sequence encoding a transmembrane domain of the wild-type WFS1 protein.

8. The transgenic mouse of claim 1, wherein said null allele lacks a nucleotide sequence encoding all transmembrane domains of the wild-type WFS1 protein.

9. The transgenic mouse of claim 1, wherein said null mutation comprises a mutation in exon 8 of wild-type WFS1-encoding gene that results in a disruption of expression of all or part of exon 8 of wild-type WFS1-encoding gene.

10. The transgenic mouse of claim 1, wherein said null mutation is a deletion of all or part of exon 8 of wild-type WFS1-encoding gene.

11. The transgenic mouse of claim 1, wherein the wild-type WFS1 gene comprises the coding sequence set forth in SEQ ID NO: 1.

12. The transgenic mouse of claim 11, wherein said null mutation comprises a mutation in exon 8 of SEQ ID NO: 1 that results in a disruption of expression of all or part of exon 8 of SEQ ID NO: 1.

13. The transgenic mouse of claim 11, wherein said null mutation is a deletion of all or part of exon 8 of SEQ ID NO: 1.

14. The transgenic mouse of claim 1, wherein said null allele comprises a chimeric gene in which WFS1 exon 8 has been replaced with a nucleic acid comprising a sequence that encodes a marker.

15. The transgenic mouse of claim 14, wherein said marker is selected from the group consisting of green fluorescent protein (GFP), β-galactosidase, luciferase, FLAG, HA and polyhistidine.

16. The transgenic mouse of claim 1, wherein said wild-type WFS1 gene is a mouse WFS1 gene.

17. The transgenic mouse of claim 1, wherein said wild-type WFS1 encoding gene is a human WFS1 gene.

18. A method of making the transgenic mouse of claim 1, said method comprising:
   i) preparing a construct for transforming a murine cell, said construct comprising a polynucleotide sequence homologous with a WFS1 gene in the murine cell to recombine with said WFS1 gene,
   ii) introducing said construct into murine embryonic stem cells;
   iii) selecting a cell from step (ii) which has incorporated into its genome said polynucleotide in a WFS1 gene in a manner that disrupts the wild-type function of said WFS1 gene to create a null mutation (null allele);
   iv) introducing said selected cell into a blastocyst;
   v) implanting said blastocyst into a host mouse to produce a chimeric mouse wherein said chimeric mouse comprises stably incorporated into its genome the null allele;
   vi) breeding said chimeric mouse to produce transgenic offspring mice containing the null allele; and
   vii) selecting an offspring mouse that is heterozygous for said disruption in said WFS1 gene.

19. A method of screening for an antidepressant agent comprising:
   i) administering a composition comprising a candidate antidepressant substance to the mouse according to claim 1, and
   ii) comparing the behavior of said mouse receiving said candidate antidepressant substance with the behavior of a mouse according to claim 1 that has not received said candidate antidepressant substance in at least one behavioral assay selected from the group consisting of a forced swim assay, a tail suspension assay, a learned helplessness assay, and a responsivity to reward assay, wherein an improvement in behavior in said at least one behavioral assay of the mouse receiving the candidate antidepressant substance as compared to the mouse not receiving the test substance is indicative of said candidate antidepressant substance being an antidepressant.

20. A method of screening for an antidepressant agent comprising:
   i) administering a composition comprising a candidate antidepressant substance to a the mouse according to claim 1, and
   ii) comparing BDNF levels of said mouse receiving said candidate antidepressant substance with BDNF levels of a mouse according to claim 1 that has not received said candidate antidepressant substance, wherein an increase in the BDNF levels of the mouse receiving the candidate antidepressant substance as compared to the mouse not receiving the test substance is indicative of said candidate antidepressant substance being an antidepressant.

21. A method of screening for an antidepressant agent comprising:
   i) administering a composition comprising a candidate antidepressant substance to the mouse according to claim 1, and
   ii) evaluating a behavior of said mouse of step (i) that correlates with vulnerability to stress in at least one behavioral assay selected from the group consisting of a forced swim assay, a tail suspension assay, a learned helplessness assay, and a responsivity to reward assay, wherein an improvement in said behavior indicates a decreased vulnerability to stress of the mouse receiving the candidate antidepressant substance is indicative of said candidate antidepressant substance being an antidepressant.

22. The method of any one of claims 19 through 21 further comprising a step of combining the antidepressant with a pharmaceutically acceptable carrier.

23. A colony of laboratory mice wherein said mice are useful in screening for antidepressant substances, said colony including the heterozygous mouse of claim 1.

24. The colony of mice according to claim 23, wherein said colony further comprises mice homozygous for a null WFS1 allele.

25. The colony of mice according to claim 23, wherein said colony further comprises mice having a wild-type WFS1 genotype.

26. A colony of mice consisting of mice according to claim 1.

27. A method of screening for an antidepressant agent comprising:
   i) administering a composition comprising a candidate antidepressant substance to the mouse according to claim 1, and
   ii) comparing the behavior of said mouse receiving said candidate antidepressant substance with the behavior of another mouse according to claim 1 that has not received said candidate antidepressant substance in a forced swim assay, wherein a decrease in immobility time of the mouse receiving the candidate antidepressant substance as compared to the mouse not receiving the test substance is indicative of said candidate antidepressant substance being an antidepressant.

28. A method of screening for an antidepressant agent comprising:
   i) administering a composition comprising a candidate antidepressant substance to the mouse according to claim 1, and
   ii) comparing the behavior of said mouse receiving said candidate antidepressant substance with the behavior of another mouse according to claim 1 that has not received said candidate antidepressant substance in the Kasahara test, wherein an increased number of turns of the water wheel by the mouse receiving the candidate antidepressant substance as compared to the mouse not receiving the test substance is indicative of said candidate antidepressant substance being an antidepressant.

29. A method of screening for an antidepressant agent comprising:
   i) administering a composition comprising a candidate antidepressant substance to the mouse according to claim 1, and
   ii) comparing the behavior of said mouse receiving said candidate antidepressant substance with the behavior of another mouse according to claim 1 that has not received said candidate antidepressant substance in a tail suspension assay, wherein a decrease in the immobility time of the mouse receiving the candidate antidepressant substance as compared to the mouse not receiving the test substance is indicative of said candidate antidepressant substance being an antidepressant.

30. A method of screening for an antidepressant agent comprising:
   i) administering a composition comprising a candidate antidepressant substance to the mouse according to claim 1, and
   ii) comparing the behavior of said mouse receiving said candidate antidepressant substance with the behavior of another mouse according to claim 1 that has not received said candidate antidepressant substance in an elevated plus maze test, wherein an improvement in performance time of the mouse receiving the candidate antidepressant substance as compared to the mouse not receiving the test substance is indicative of said candidate antidepressant substance being an antidepressant.

31. A method of screening for an antidepressant agent comprising:
   i) administering a composition comprising a candidate antidepressant substance to the mouse according to claim 1, and
   ii) comparing the behavior of said mouse receiving said candidate antidepressant substance with the behavior of another mouse according to claim 1 that has not received said candidate antidepressant substance in a learned helplessness assay, wherein an improvement in escaping avoidable shock by the mouse receiving the candidate antidepressant substance as compared to the mouse not receiving the test substance is indicative of said candidate antidepressant substance being an antidepressant.

32. A method of screening for an antidepressant agent comprising:
   i) administering a composition comprising a candidate antidepressant substance to the mouse according to claim 1, and
   ii) comparing the behavior of said mouse receiving said candidate antidepressant substance with the behavior of another mouse according to claim 1 that has not received said candidate antidepressant substance in a responsivity to reward assay, wherein an increase in responsivity to rewards by the mouse receiving the candidate antidepressant substance as compared to the mouse not receiving the test substance is indicative of said candidate antidepressant substance being an antidepressant.

* * * * *